United States Patent
Horn

(10) Patent No.: US 11,648,247 B1
(45) Date of Patent: May 16, 2023

(54) COMPOSITIONS AND METHODS FOR THE TREATMENT OF PRESBYOPIA

(71) Applicant: Lenz Therapeutics, Inc., Rancho Santa Fe, CA (US)

(72) Inventor: Gerald Horn, Deerfield, IL (US)

(73) Assignee: Lenz Therapeutics, Inc., Rancho Santa Fe, CA (US)

( * ) Notice: Subject to any disclaimer, the term of this patent is extended or adjusted under 35 U.S.C. 154(b) by 0 days.

(21) Appl. No.: 17/552,654

(22) Filed: Dec. 16, 2021

(51) Int. Cl.
| | |
|---|---|
| *A61K 31/498* | (2006.01) |
| *A61K 31/439* | (2006.01) |
| *A61P 27/10* | (2006.01) |
| *A61K 47/10* | (2017.01) |
| *A61K 47/36* | (2006.01) |
| *A61K 47/02* | (2006.01) |
| *A61K 47/40* | (2006.01) |

(52) U.S. Cl.
CPC .......... *A61K 31/498* (2013.01); *A61K 31/439* (2013.01); *A61K 47/02* (2013.01); *A61K 47/10* (2013.01); *A61K 47/36* (2013.01); *A61K 47/40* (2013.01); *A61P 27/10* (2018.01)

(58) Field of Classification Search
CPC .... A61K 41/439; A61K 31/498; A61K 47/10; A61K 47/36; A61P 27/10
See application file for complete search history.

(56) References Cited

U.S. PATENT DOCUMENTS

| | | | |
|---|---|---|---|
| 4,474,751 A | 10/1984 | Haslam et al. | |
| 4,906,467 A | 3/1990 | Schwartzman et al. | |
| 6,291,466 B1 | 9/2001 | Gwon et al. | |
| 6,353,022 B1 | 3/2002 | Schneider et al. | |
| 6,410,544 B1 | 6/2002 | Gwon et al. | |
| 8,299,079 B2 | 10/2012 | Kaufman | |
| 8,455,494 B2 | 6/2013 | Kaufman | |
| 8,501,800 B2 | 8/2013 | Bowman et al. | |
| 9,089,562 B2 | 7/2015 | Horn et al. | |
| 9,314,427 B2 | 4/2016 | Horn et al. | |
| 9,320,709 B2 | 4/2016 | Horn et al. | |
| 9,833,441 B2 | 12/2017 | Horn et al. | |
| 9,844,537 B2 | 12/2017 | Horn et al. | |
| 9,968,594 B2 | 5/2018 | Horn et al. | |
| 10,052,313 B2 | 8/2018 | Horn et al. | |
| 10,064,818 B2 | 9/2018 | Horn et al. | |
| 10,307,408 B2 | 6/2019 | Horn et al. | |
| 10,617,763 B2 | 4/2020 | Horn et al. | |

(Continued)

FOREIGN PATENT DOCUMENTS

| | | |
|---|---|---|
| WO | 2002/100437 A2 | 12/2002 |
| WO | 2009/077736 A2 | 6/2009 |

(Continued)

OTHER PUBLICATIONS

Drance, S.M., Dose response of human intraocular pressure to aceclidine, Arch Ophthalmol, Oct. 1972;88(4):394-6.

(Continued)

*Primary Examiner* — Timothy P Thomas
(74) *Attorney, Agent, or Firm* — Wood, Phillips, Katz, Clark & Mortimer

(57) ABSTRACT

The present invention is directed to compositions for and methods for the treatment of presbyopia comprising from about 0.3% to about 2.0% w/v aceclidine and from about 0.07% to about 0.15% w/v brimonidine.

5 Claims, 5 Drawing Sheets

(56) References Cited

U.S. PATENT DOCUMENTS

| | | |
|---|---|---|
| 10,959,990 B2 | 3/2021 | Horn |
| 11,179,327 B2 | 11/2021 | Horn et al. |
| 11,179,328 B2 | 11/2021 | Horn |
| 2002/0036264 A1 | 3/2002 | Nakasuji et al. |
| 2003/0104996 A1 | 6/2003 | Li et al. |
| 2003/0165545 A1 | 9/2003 | Huth et al. |
| 2003/0232089 A1 | 12/2003 | Singh et al. |
| 2004/0106644 A1 | 6/2004 | Randazzo |
| 2005/0196370 A1 | 9/2005 | Yu et al. |
| 2006/0177430 A1 | 8/2006 | Bhushan |
| 2007/0297990 A1 | 12/2007 | Shah et al. |
| 2009/0074786 A1 | 3/2009 | Dor et al. |
| 2010/0016395 A1 | 1/2010 | Benozzi |
| 2010/0310476 A1 | 12/2010 | Tamarkin et al. |
| 2011/0172302 A1 | 7/2011 | Dalton et al. |
| 2011/0251285 A1 | 10/2011 | Tien et al. |
| 2012/0094962 A1 | 4/2012 | Skulachev |
| 2012/0165295 A1 | 6/2012 | Painter et al. |
| 2013/0245030 A1 | 9/2013 | Kaufman |
| 2016/0018671 A1 | 1/2016 | Waite et al. |
| 2019/0038609 A1 | 2/2019 | Horn |
| 2019/0240152 A1 | 8/2019 | Horn et al. |
| 2020/0188369 A1 | 6/2020 | Horn |
| 2020/0281906 A1* | 9/2020 | Horn .................... A61K 31/439 |

FOREIGN PATENT DOCUMENTS

| | | |
|---|---|---|
| WO | 2010/135731 A1 | 12/2010 |
| WO | 2013/041967 A2 | 3/2013 |

OTHER PUBLICATIONS

Grunberger, J., et al., The pupillary response test as a method to differentiate various types of dementia, Neuropsychiatr, 2009, 23(1), 52-57.

Ward, J.S., et al., 1,2,5-Thiadiazole analogues of aceclidine as potent m1 muscarinic agonists, J Med Chem, Jan. 29, 1988, 41(3), 379-392.

Berge, S. M., et al., "Pharmaceutical Salts", Journal of Pharmaceutical Science, 1977, 66, 1-19.

Hoyng, F.J., The combination of guanethidine 3% and adrenaline 0.5% in 1 eyedrop (GA) in glaucoma treatment, Br J Ophthalmol, Jan. 1979, 63(1), 56-62.

Romano, J.H., Double-blind cross-over comparison of aceclidine and pilocarpine in open-angle glaucoma, Br J Ophthalmol, Aug. 1970, 54(8), 510-21.

Smith, S.A., Subsensitivity to cholinoceptor stimulation of the human iris sphincter in situ following acute and chronic administration of cholinomimetic miotic drugs, Br J Pharmacol, Jul. 1980, 69(3), 513-8.

Tataru, C.P., Antiglaucoma pharmacotherapy, J Med Life, Sep. 15, 2012, 5(3), 247-51.

Glaucadrine, poudre et solvant pour collyre en solution, botte de 1 aeon de lyophilisat + acon de solvant de 10 ml GI http://www.doctissimo.fr/medicament-GLAUCADRINE.htm Machine Translation Provided.

Bijsluiter: Glaucocare https://consumed.nl/bijsluiters/glaucocare Machine Translation Provided.

Glaunorm toma all'Indice farmaci http://www.anibaldi.eu/farmaci/schedetecniche/GLAUNORM.html Machine Translation Provided.

N.F. Muller and R.P. Dessing (Eds.) 4th Edition, European Drug Index, European Society of Clinical Pharmacy, Deutscher Apotheker Verlag Suttgart 1997, p. 550.

Akorn Incorporated MSDS:Tropicacyl (R): Rev 11-11.

Mayo Clinic: Tropicamide (Opthalmic Route), 2015, https://www.mayocllinic.org/drugs-supplements/tropicamide-ophthalmic-route/description/drg-20066481.

Chung S.T. et al., The effect of dioptric blur on reading performance, Vision Res, Jun. 2007, 47(12), 1584-94.

Cowan E.C., et al., Clinical evaluation of a new mydriatic-mydrlate, Br J Ophthalmol, Dec. 1962, 46(12), 730-6.

Davidson,S., General medicine and visual side effects, Br Med J, Mar. 24, 1979, 1(6166), 821.

Edwards, R.S., Behaviour of the fellow eye in acute angle-closure glaucoma, Br J Ophthalmol, Sep. 1982, 66(9), 576-9.

Gardiner, P.A., ABC of Ophthalmology: Methods of examination, Br Med J, Dec. 9, 1978, 2(6152), 1622-6.

Gardiner, P.A., ABC of Ophthalmology: accidents and first aid, Br Med J, Nov. 11, 1978, 2(6148), 1347-50.

Mohan, K., Optimal dosage of cyclopentolate 1% for cycloplegic refraction in hypermetropes with brown irides, Indian J Ophthalmol, Nov.-Dec. 2011, 59(6), 514-6.

Nayak, B.K., A comparison of cycloplegic and manifest refractions on the NR-1000F (an objective Auto Refractometer), Br J Ophthalmol, Jan. 1987, 71(1), 73-5.

Park, J.H., The comparison of mydriatic effect between two drugs of different mechanism, Korean J Ophthalmol, Mar. 2009, 23(1), 40-2.

Frinavarat, A., Effective pupil dilatation with a mixture of 0.75% tropicamide and 2.5% phenylephrine: A randomized controlled trial, Indian J Ophthalmol, Sep.-Oct. 2009, 57(5), 351-4.

Wood, J.M., Pupil dilatation does affect some aspects of daytime driving performance, Br J Ophthalmol, Nov. 2003, 97(11), 1387-90.

Fechner, P.U., et al., Accomodative effects of aceclidine in the treatment of glaucoma, Amer J Ophth. Jan. 1975., 79(1) 104-106.

Latanoprost label (Year:2006).

Varma et al., Concentration of Iatanoprost Ophthalmic Solution after 4 to 6 Weeks Use in an Eye Clinic Setting, Glaucoma, vol. 47, Issue 1, Jan. 2006.

Glaucostat, Prospecto/Ficha Tecnica IPC 11-83 Tracer No. GCS-E-18595 05/00 Machine Translation Provided.

Mayama, et al. Myopia and Advanced-Stage Open Angle Glaucoma 2002 by American Academy of Ophthalmology, Inc. ISSN 0161-6402/02, Published by Elsevier Science Inc. pp. 2072-2077.

\* cited by examiner

COMPOSITIONS AND METHODS FOR THE TREATMENT OF PRESBYOPIA

BACKGROUND OF THE INVENTION

As a person ages the minimum distance from the eye at which an object will come into focus, provided distance vision is corrected or is excellent unaided, increases. For example, a 10-year-old can focus on an object or a "focal point" only three inches (0.072 meters) from their eye while still retaining excellent distance vision; a 40-year-old at six inches (0.15 meters); and a 60-year-old at an inconvenient 39 inches (1.0 meter). This condition of increasing minimum focal length in individuals with excellent unaided distance vision is called presbyopia, loosely translated as "old-man eye".

Excellent unaided distance vision is also known as emmetropia. The inability to focus on distant focal points is known as myopia and the inability to focus on near focal points is known as hyperopia. Specifically, "distance" vision is considered any focal point 1 meter or more from the eye and near vision is any focal point less than 1 meter from the eye. The minimum focal length at which an object will come into focus is known as the "near point". The change in focus from distance to the near point and any focal point in between is called accommodation. Accommodation is often measured in diopters. Diopters are calculated by taking the reciprocal of the focal length (in meters). For example, the decrease in accommodation from a 10-year-old eye to a 60-year-old eye is about 13 diopters ($1 \pm 0.072$ meters=13.89 diopters; $1 \pm 1$ meter=1 diopter).

The highest incidence of first complaint of presbyopia occurs in people ages 42-44. Presbyopia occurs because as a person ages the eye's accommodative ability which uses near reflex-pupil constriction, convergence of the eyes and particularly ciliary muscle contraction, decreases. This reduction in accommodation results in an inadequate change in the normal thickening and increased curvature of the anterior surface of the lens that is necessary for the shift in focus from distant objects to near objects. Important near focus tasks affected by presbyopia include viewing computer screens (21 inches) and reading print (16 inches).

Presbyopia is a normal and inevitable effect of ageing and is the first unmistakable sign for many in their forties that they are getting older. One study found that more than 1 billion people worldwide were presbyopic in 2005. This same study predicted that number to almost double by the year 2050. If everyone over the age of 45 is considered to be presbyopic, then an estimated 122 million people in the United States alone had presbyopia in 2010. As baby boomers reach the critical age, this number is only going to increase.

Presbyopia carries with it a stigma resulting from the limitation in ability to quickly function at many tasks requiring focusing at both distant and near points, which once occurred almost immediately. In the presbyopic patient, these tasks can be performed only by the use of eyeglasses, contact lenses or after undergoing invasive surgery. One such optical modification, the monovision procedure, can be executed with the use of glasses, contact lenses or even surgery. The monovision procedure corrects one eye for near focus and the other eye for distance focus. However, monovision correction is normally accompanied by loss of depth perception and distance vision particularly in dim light (e.g. night). Other surgical procedures that have been developed to relieve presbyopia include: (1) the implantation of intraocular lenses (INTRACOR® presbyopia treatment surgery; registered trademark of Technolas Perfect Vision GMBH); (2) reshaping of the cornea (PresbyLASIK presbyopia treatment surgery and conductive keratoplasty); (3) scleral band expansion; and (4) implantation of corneal inlays (Flexivue Microlens® corneal inlays; registered trademark of PresbiBio LLC, Kamra®; registered trademark of AcuFocus, Inc. and Vue+). Kamra® corneal inlays manufactured by AcuFocus work by inlaying a pinhole on the cornea to increase the depth of focus.

A similar effect can be achieved with general miotic agents, such as pilocarpine (a non-selective muscarinic acetylcholine receptor agonist), carbachol (a non-selective muscarinic acetylcholine receptor agonist), and phospholine iodide (an acetylcholinesterase inhibitor). These general miotics can induce a pinhole pupil at sufficient concentrations to achieve pupils below 2.0 mm and potentially extend depth of focus much like an inlay, but at concentrations sufficient to cause pinhole pupil diameters of 2.0 mm or less these agents trigger increased ciliary muscle contraction and induce accommodation of any remaining reserves, improving near vision at the expense of distance vision in individuals who still retain some accommodative function. The side effects of ciliary spasm induced migraine like brow pain and blurred distance vision from induced myopia beyond the ability of a pinhole pupil to correct then necessitate using weaker concentrations with much shorter acting and more marginal effect, such as found with pilocarpine. In such cases even slight hyperopia helps offset the induced myopia while even very small increments of myopia, which is very common, exacerbate it. In extreme cases, such ciliary muscle spasms may possibly be associated with anterior chamber shallowing and pull on the ora serrata of the retina, resulting in a retinal tear and or retinal detachment.

Miotic agents have been described in various patent and patent applications for the treatment of presbyopia. U.S. Pat. Nos. 6,291,466 and 6,410,544 describe the use of pilocarpine to regulate the contraction of ciliary muscles to restore the eye to its resting state and potentially restore its accommodative abilities.

U.S. Pat. No. 8,524,758 describes the use of pilocarpine with the non-steroidal anti-inflammatory, diclofenac, to reduce brow ache from ciliary spasm and increase the time in which the ciliary muscle contraction is regulated. International PCT Application Publication WO/2013/041967 describes the use of pilocarpine with oxymetazoline or meloxicam to temporarily overcome ocular conditions such as presbyopia.

U.S. Pat. No. 8,299,079 (HEK Development LLC) describes the use of direct acting general miotic agents such as pilocarpine, carbachol and phospholine iodide with the alpha 2 selective vasoconstrictor brimonidine at a concentration of 0.3% or less. However, the use of brimonidine concentrations of about 0.20% w/v induces ciliary spasm with often migraine intensity brow and/or headaches, and frequently results in increased rebound hyperemia. For example, rebound redness occurs in 25% of patients using brimonidine 0.20% w/v (Alphagan® brimonidine tartrate ophthalmic solution, registered trademark of Allergan, Inc.) twice daily.

US Patent Application Publication No. 2014/0113946 describes the use of pilocarpine with the alpha 1 and mild alpha 2 agonist vasoconstrictor oxymetazoline, demonstrating limitations in distance sharpness and duration, whereby a cohort largely restricted to mild hyperopes is required to neutralize the induced myopia (Table 5). Of the 16 eyes treated only three were −0.25 to −0.50 diopters, and eight were mildly hyperopic. Of the −0.50 diopter eyes two were reduced to 20.40 distance. Further, duration was limited as full effect became diminished in about four hours. Pupil size range was from 2.0 mm to 2.7 mm, where enhanced near effect and distance sharpness from depth of focus was minimal to absent.

These attempts at miotic treatment for presbyopia all induce transient myopia of several diopters reducing distance vision to about legal blindness or worse at the expense of improved near vision for the full duration of their action, typically lasting several hours. This myopic effect is amplified by the exponential drop off in distance acuity with even small increments of nominal myopia in terms of unaided untreated vision. For example, a person having mild myopia (e.g. spherical equivalents of −0.25 D, −0.50 D) that is usually associated with glasses free distance vision, typically will have several lines of distance vision loss after instillation of pilocarpine 1% (i.e. spherical equivalent of −0.75 D.).

Miotics historically used to treat glaucoma, other than pilocarpine, particularly aceclidine, are also associated with ciliary spasm, brow and/or headache, and myopic blur. Further, aceclidine is unstable in solution. Normally, aceclidine is stored in a two-bottle system; one bottle containing the lyophilized aceclidine and the second bottle containing the diluent necessary to reconstitute the lyophilized aceclidine before topical instillation. However, the primary issue with its use as a presbyopic miotic is the attendant pain and in some cases distance blur that may be induced.

Thus, there is a need in the art for a treatment of presbyopia that is non-invasive and convenient with minimal side effects. Specifically, there is a need for an ophthalmological composition that will allow a person suffering from presbyopia to focus on near objects without significant side effects such as diminished distance vision, blurred vision, pain, redness, impaired night driving or incapacitating dim light vision, induced nasal congestion, or risk of retinal detachment. Further, there is a need in the art for a reduction or elimination of the need for a cycloplegic agent to be used with aceclidine and still enhance duration and efficacy over aceclidine alone.

SUMMARY OF THE INVENTION

In certain embodiments, the present invention is directed to compositions for the treatment of presbyopia comprising from about 0.3% to about 2.0% w/v aceclidine and from about 0.07% to about 0.15% w/v brimonidine.

In certain other embodiments, the present invention is directed to methods of treating presbyopia comprising administering a composition comprising from about 0.3% to about 2.0% w/v aceclidine and from about 0.07% to about 0.15% w/v brimonidine to a subject in need thereof.

In a preferred embodiment, the compositions of the present invention further comprise one or more surfactants and or one or more viscosity agents.

DETAILED DESCRIPTION OF THE INVENTION

Figure 1:
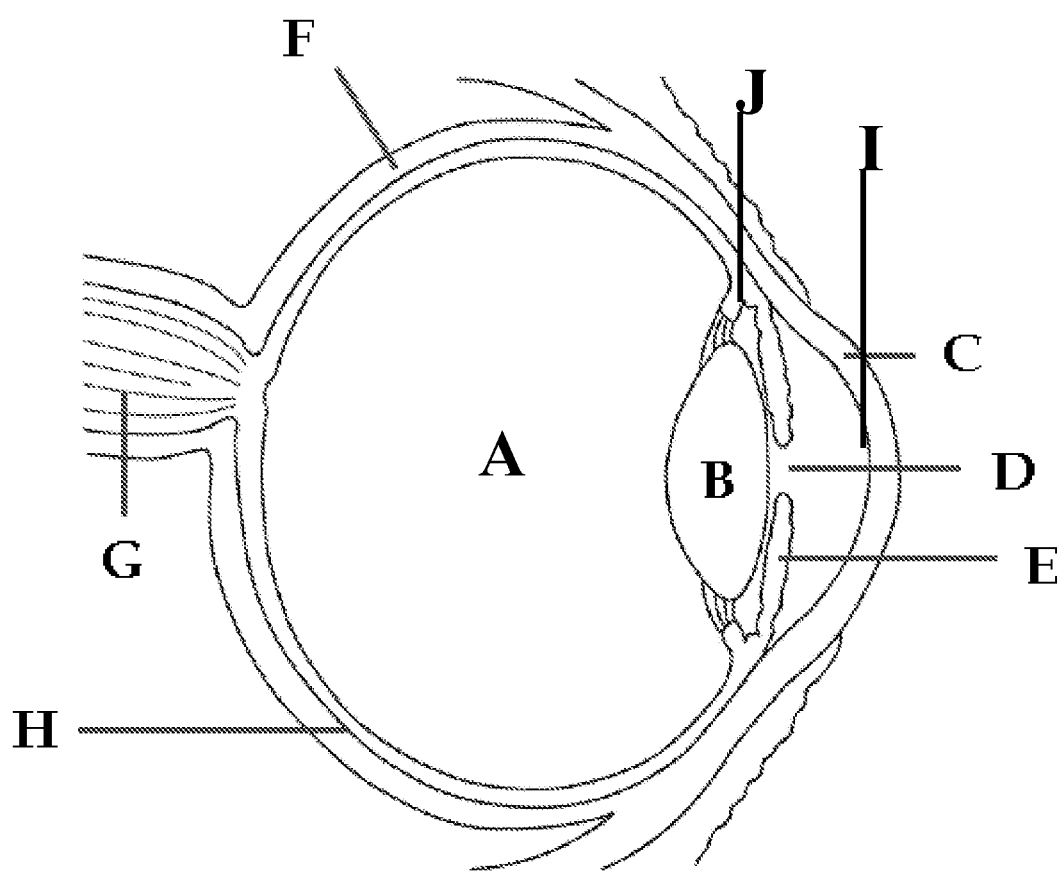
FIG. 1 is a graphical representation of the human eye.

It has surprisingly been discovered that the addition of from about 0.07% to about 0.15% w/v or less brimonidine to compositions comprising aceclidine, prolongs the duration of miotic effect provided by aceclidine leading to prolonged surface residence time and greater intraocular penetration and intraocular absorption. It is further observed that concentration of brimonidine above 0.15% w/v causes significant trigger of the alpha 1 receptor leading to ischemia and rebound redness, which neutralizes the benefit of the prolonged duration at concentrations from about 0.07% to about 0.15% w/v brimonidine.

Another surprising discovery of the present invention, is that when the pH of a composition comprising a muscarinic agonist and brimonidine is below about 6.0 the duration of miosis is prolonged up to 14 hours.

Further, because brimonidine is at a concentration from about 0.07% to about 0.15% w/v the subject experiences very little to no incidence of tachyphylaxis or rebound hyperemia.

The present invention is directed to compositions and methods of treating presbyopia, comprising administering to a patient in need thereof a pharmaceutical composition comprising from about 0.3% to about 2.0% w/v, preferably from about 1.0% to about 2.0% w/v aceclidine and from about 0.07% to about 0.15% w/v brimonidine, preferably from about 0.07% to about 0.10% w/v, more preferably from about 0.07% to about 0.09% w/v and most preferably about 0.075% or 0.08% w/v.

In another preferred embodiment, compositions of the present invention further comprise one or more surfactants and or one or more viscosity agents.

The compositions and methods of the present invention treat presbyopia by improving depth of focus in patients with presbyopia by administering an ophthalmological composition to the eye that reduces pupil dilation in the dark or in dim light, produces a particular degree and duration of miosis without accommodation, provides cosmetic whitening and/or induce redness prophylaxis. The compositions and methods of the present invention also do not cause significant pupil rebound, tachyphylaxis, ciliary spasms, induction of myopia or reduction in distance vision. Additionally, the compositions and methods of the present invention allow for the further improvement in visual acuity and depth perception of binocular (both eyes) treatment. The ophthalmological composition of the present invention surprisingly creates a pupil of from about 1.5 to about 2.4 mm at the anterior iris plane and about 2.0 mm at the corneal surface. Not wishing to be held to particular theory the clinical effect appears to involve both with modulated increase in accommodative tone and enhanced pinhole near depth of focus for improved near vision, estimated to be about −1.25 D or less, but restricted in power to remain within the range of pinhole correction for distance, found to be about −1.00 D or less creating a sum increase that may in some cases create a near vision add of +2.00 D or more without distance blur; and with a reduction or ablation of the redness that is otherwise a hallmark of the use of miotic agents. The pupil miosis of the present invention with such modulation and restriction of peak accommodative tone is superior to the pinhole effect of the Kamra® corneal inlays and Flexivue Microlens® corneal inlays, allowing binocular treatment without peak dimming. Pupil miosis of the present invention with modulated accommodation is also superior to inlays because the constriction of the actual pupil does not result in the attendant severe night vision disturbance caused by the light scattering borders of the pre-corneal pinholes created by the inlays. Further pupil miosis provides a greater field of vision and transmission of more focused light, and in a discovered optimal pupil range of about 1.5 mm to 2.1 mm using formulation discoveries of the present invention does so with negligible to mild and very tolerable dimming and enhanced contrast, distance vision, reduced glare at night, and improved near vision.

Conventional formulations of pilocarpine and carbachol, in order to affect any reasonable duration of effect, are still restricted to less than or equal to about 4 hours in most cases, as the high ratio of accommodation to pupillary miosis requires minimal concentrations of pilocarpine of about 1.0% to minimize but not eliminate distance induced myopic blur and ciliary spasm. Further pilocarpine must be instilled monocularly to minimize intolerable distance blur to a still bothersome 2-3 lines of distance blur. Even instilled monocularly, pilocarpine still may create bothersome attendant distance blur and must be restricted to about 1.0%. Upon instillation of 1.0% pilocarpine pupil size is about 2.3 mm or larger in most subjects and thereby restricts any significant pinhole depth perception benefit as well as any pinhole filtering of induced myopic rays. The restriction to about 1.0% for these conventional formulations of pilocarpine with the attendant short duration and still bothersome but reduced distance blur in emmetropes or myopes (somewhat neutralized in low hyperopes) are attempts to prevent extremely strong accommodation of 5 D to 11 D well known to occur at higher concentrations of pilocarpine.

Without wishing to be held to particular theory, the improvement in duration by adding brimonidine to a muscarinic agonist, particularly a miotic, is related to brimonidine's transiently induced miosis of 1.0-2.0 mm. However, the miotic effect of brimonidine is typically of about four hours duration, and often tachyphylactic, with rebound mydriasis also seen with daily instillation over several weeks at 0.15%. Edwards, J D et al., Effect of brimonidine tartrate 0.15% on night-vision difficulty and contrast testing after refractive surgery, *J Cataract Refract Surg.* 2008 September; 34(9):1538-41. It is a theory of the present invention that the vasodilation caused by miotics including but not limited to aceclidine, pilocarpine, and carbachol creates a surface plexus of dilated microvessels, particularly post capillary venules, that allows substantial egress from the ocular surface within this vascular network out of the eye. At concentrations as low as 0.001% vasoconstriction of these vessels has been found to occur, and, while at higher concentrations alpha 1 receptor recruitment at a 1:900 ratio versus alpha 2 becomes significant, and as the alpha 1 receptors once stimulated are potent vasoconstrictors of larger arterioles, increases the likelihood of rebound dilation.

Therefore, it is a theory of the present invention that an ideal concentration of range for brimonidine, the lowest concentration being consistent with selective microvessel constriction, and the highest below the level of significant rebound dilation, is required for optimized prolongation on the ocular surface for any miotic. That range is virtually estimated to be from about 0.001% to about 0.15% w/v, more preferably from about 0.001% to about 0.08% w/v, and most preferably from about 0.07% to about 0.08% w/v, significantly above or below which duration will not be as effectively extended.

Still further, aceclidine in a preferred vehicle including brimonidine has been found to extend the duration of miosis to beyond 5 hours, typically 6-7 hours of efficacy for near depth of field improvement at pupil sizes of 1.5 to 2.0 mm, and beyond 7 hours, typically 10-12 hours or longer with the addition of brimonidine at 0.07% to 0.08%. In a still further embodiment lower pH is virtually found to cause the formulation to remain on the ocular surface longer, and therefore provide more sustained microvessel constriction and reduced egress of active ingredients. At for example a pH of 5.4 brimonidine is about 2 log units below its pKa, and virtually all drug is ionized with minimal corneal or vascular absorption.

The extent of enhanced duration realized by combining brimonidine at concentrations from about 0.07% to about 0.15% with miotics, far exceeds the transient miosis of 3-4 hours.

It is further believed that darker irises, particularly brown irises, retard the penetration of miotic agents, particularly aceclidine and pilocarpine, due to greater density of lipophilic pigment. The effectiveness of these miotics in brown irises is therefore greatly enhanced by both the increase of residence time, corneal penetration and intraocular absorption created by combining brimonidine at concentrations from about 0.07% to about 0.15% with aceclidine or other miotics.

Further, due to the apparent and surprisingly selective nature of aceclidine, and the commercially stable aceclidine formulation discoveries of the present invention, administration to the eye of compositions of the present invention result in a net strongly enhanced near vision acuity from both pupil miotic pinhole effect and moderate modulated ciliary accommodation. These beneficial effects are accompanied by a filtering pupil effect, which eliminates any distance blur from the accommodation, correcting residual refractive error and optical aberrations as may exist to in many cases improve distance vision as well. Thus, the administration of aceclidine results in pupil miosis without excessive accommodation and attendant distance blur.

However, aceclidine alone may cause substantial redness and brow ache in some individuals. Without formulation enhancement of the present invention, aceclidine may produce either less than optimal pupil miosis at low concentrations or at higher concentrations require more than desired peak miosis to attain satisfactory duration of greater than 3-4 hours. Further, aceclidine without formulation enhancements of the present invention causes dimming of vision in dim or absent lighting as well as ciliary pain above a reasonably tolerable threshold that may last for an hour or more and be similar to a severe migraine headache.

Certain embodiments of the present invention enhance the discovered preferred degree of pupillary miosis by providing a consistent range of effect of about 1.50-2.20 mm for most patients using a preferred embodiment of a nonionic surfactant and viscosity agent. Similar benefit may be achieved using other permeation enhancers, particularly hydroxypropylmethyl cellulose, high viscosity carboxymethyl cellulose, Carbopol® (polyacrylic acid or carbomer), and various viscosity additives that increase drug residence time, such as xanthan gums, guar gum, alginate, and other in situ gels well known to experts in the art. It is well known to experts in the art that the exact concentration of a specific viscosity agent will depend on both the molecular weight for that agent selected and the concentration, such that for increased molecular weight a reduced concentration can have the same viscosity. The present invention further prevents nasal congestion otherwise occurring when substantial aceclidine levels reach the nasal mucosa, due to the rheologic properties of the preferred embodiment.

The combination of aceclidine and a low concentration of a selective α-2 adrenergic receptor agonist (α-2 agonist or α-2 adrenergic agonist), such as fadolmidine, brimonidine or guanfacine, allows for the desired miotic effect with diminished or no redness. The use of low concentrations of a selective α-2 agonist results in substantial reduction of hyperemia with greatly reduced risk of rebound hyperemia that is found in concentrations of about 0.06% w/v or more. Furthermore, the use of low concentrations of selective α-2 agonist does not adversely modify the pupil constriction caused by aceclidine. In contrast, the use of brimonidine 0.20% w/v, when topically applied for pupil modulation for night vision, result in tachyphylaxis of pupil modulation due to α-2 receptor upregulation in almost 100% of treated subjects within four weeks of use.

It is surprisingly discovered that adding a viscosity agent to compositions described above only modestly improves magnitude and duration, however when first adding a nonionic surfactant, such as polyoxyl stearate or polysorbate 80, optimal concentrations are discovered that provide greatly improved magnitude and duration for the present invention, to which viscosity may then provide added duration much more substantially than when added alone. For polysorbate 80 or polyoxyl 40 stearate concentrations of 1.0% to 10.0%, and more preferably about 2.5% to 5.0% w/v have been found to be beneficial.

The longest residence time and longest duration of effect for the subject invention results when particular nonlinear viscosity to shear viscosity ratios are reached. It is a discovery of the present invention that compositions containing nonionic surfactants at a concentration from about 1% to about 5% w/v and viscosity agents such as HPMC at a concentration from about 0.5% to about 1.4% w/v and brimonidine at concentrations from about 0.07% to about 0.15% w/v maximize residence time.

Not wishing to be held to particular theory citrate in combination with EDTA as a preferred embodiment buffer appears to 1) reduce redness; 2) enhance sorbate preservative shelf life, and in combination of the above with BAK 0.005% to 0.02% (0.02% preferred) further enhances near vision lines to about 4 lines and duration to about 8 to 12 hours.

In a preferred embodiment, compositions of the present invention further comprise sodium chloride, preferably at a concentration from about 0.5% to about 1.5% w/v, more preferably from about 0.65% to about 0.9% w/v. Optionally, sodium chloride may be substituted with boric acid, preferably at 0.35% or potassium borate, preferably at 0.47%;

Not wishing to be held to particular theory, it appears the addition of nonionic surfactant at optimized concentration of about 2.0% to about 7.0% enhances permeation of aceclidine into the eye, which may relate to optimal micellar size particularly once of micromicellar or nanomicellar range. This increased permeation coincides with the desirable increase in magnitude and duration and absent tropicamide but in the presence of mannitol with slight increases in ciliary sensation and dimming. Therefore, in the presence of the combined formulation enhancements above, where a cycloplegic agent is no longer required, addition of a nonionic surfactant at concentrations found to be preferred may be further improved with much lower concentrations of a cycloplegic agent than those found in U.S. Pat. No. 9,089,562, such as the use of about 0.042% tropicamide with aceclidine 1.40%. For the present invention then preferred embodiments include aceclidine of about 1.75%, mannitol 2.5%, polysorbate 80 of about 2.5% to 5.0%, CMC of about 1.42%, or HPMC of about 1.8% and tropicamide of about 0.004%-0.010%, more preferably about 0.005% to 0.007%, and most preferably about 0.005%-0.006%. Micelle formation above the critical micellar concentration may allow for micelles to spread across the tear film surface and spread at low concentrations to cover this surface, while at higher concentrations these micelles becoming increasingly contracted and "squeezed" along the surface. Not wishing to be held to particular theory, it is believed at an optimal concentration a minimal micelle diameter is achieved before significant multiple lamellae (layering) occurs. It is believed that at the optimal concentration nanomicelles of about 100 to 250 nm along the surface are achieved surrounding the highly charged and hydrophilic aceclidine, facilitating its penetration through the very lipophilic epithelium;

Not wishing to be held to particular theory, the addition of polysorbate 80 4.0% or BAK 0.02% to sorbate about 0.10%, EDTA about 0.10%, in a preferred composition of aceclidine 1.75%, mannitol 2.5%, and citrate buffer (1 to 100 mM 3-5 mM preferred) is above the critical micellar concentration of polysorbate 80 or BAK such that either may reduce nucleophile collisions and supports cold chain stability. BAK, being a cationic surfactant, and BAK micelles, creating an ionic micellar gradient with + charge NH4+ quaternary nitrogen bring on the polar heads aggregating outside and lipophilic alkyl chain on the hydrophobic tails aggregating on the inside may cause significant similar aceclidine alignment due to its dipole with quaternary NH3 nucleophilic or NH4 protonated nitrogens oriented along the outside polar heads and more hydrophobic carbonyls C=O along hydrophobic BAK micellar tails these preventing, greatly reducing, or moderately reducing collisions of any nonionic aceclidine molecules—the nucleophiles—which if oriented in solution such that randomly they collide with another aceclidine carbonyl will result in chemical conversion of that aceclidine via nucleophilic attack at its targeted carbonyl, which can recur from such nucleophiles to other aceclidines so oriented repeatedly and cause loss of stability without such BAK orientation via 0.005% and preferably 0.01% to 0.02% most preferred micelles. The concentration of such nonionic nucleophiles at a preferred pH in the preferred embodiment is relatively low, but the ability of these nonionic nucleophiles to destabilize adjacent aceclidines repeatedly without themselves degrading is otherwise high. The result may be improved potency for 1 month plus of a mixed solution once opened in a dual chamber bottle and mixing occurs of lyophilized aceclidine/mannitol with the remainder of the formulation in the diluent and or improved stability sufficient for commercialization in solution, either at room temperature or via cold chain;

It is discovered that BAK alone does not provide sufficient bacterial and fungal preservative efficacy but that BAK and sorbate, or sorbate alone satisfactorily preserve diluent and or mixed solutions of the invention;

Not to be wishing to be held to particular theory preferred embodiments of the present invention such as containing 1.25% hydroxypropyl methyl cellulose may have a viscosity of about 400 cps prior to instillation, yet unlike conventional high viscosity artificial tear formulations such as Celluvisc® lubricant eye drops at about 400 cps, which may blur vision for 10-20 minutes or Liquigel® lubricant eye gel drops at about 100 cps, which causes similar but slightly reduced blurring causes only about 60 seconds of blur dissipating rapidly with an influx of tear secretion; where both a nonnewtonian reduction in viscosity at high shear (such as about 1/1000 sec during a blink, and aceclidine parasympathetic trigger of tear secretion as a sialogen may contribute.

General miotic agents, such as pilocarpine, carbachol and phospholine diesterase, are capable of causing pupil miosis resulting in improved near vision of presbyopic patients. However, there is an inverse reduction in distance vision associated with these general miotic agents from miosis at peak effect and accommodation that is not seen with aceclidine. The co-administration of a cycloplegic agent with aceclidine surprisingly results in an attenuation of this reduction in distance vision.

Comfort, safety, and efficacy of a preferred embodiment of an ophthalmological composition of the present invention results from the presence of a nonionic surfactant, such as cyclodextrin alpha, beta, or gamma chains, preferably 2-hydroxypropyl beta-cyclodextrin ("HPβCD"), and, sulfobutyl ether derivative of β-cyclodextrin (Captisol®), a polyoxyl alkyl such as polyoxyl 40 stearate and polyoxyl 35 castor oil, or a poloxamer such as poloxamer 108 and poloxamer 407, a polysorbate such as polysorbate 80 or Brij® 35 polyoxyethylene glycol alkyl ether (Brij is a registered trademark of Uniqema Americas LLC); a viscosity enhancing agent, such as carboxymethyl cellulose ("CMC"); a tonicity adjustor, such as sodium chloride; a preservative, such as benzalkonium chloride and a pH from about 5.0 to about 8.0. Further, an increase in the concentration of the nonionic surfactant may result in reduced redness. Specifically, increasing polysorbate from 0.10% to 0.50-1.0% results in reduced redness. Further, increasing CMC or Carbopol® 940 polymer gel thickening agent from 0.50% to 1.5% w/v (preferably 1.40-1.43% w/v) results in enhanced near vision, both quantitative improvement and duration improvement.

The viscosity of compositions of the present invention comprising a viscosity agent may be about 25 cps or more at 25° C. and 0 shear, more preferably from about 50 to about 10,000 cps, even more preferably from about 100 to about 5,000 cps and most preferably from about 150 to about 450 cps. As a result of the shear force applied to the composition as it exits the device used for administration the viscosity may be lowered to a range from about 1 to about 25 cps at the high shear of blinking, and 50 cps to 200 cps at the low shear between blinks, allowing greater drop retention with less spillage and less nasolacrimal drainage and systemic absorption upon topical instillation.

Definitions

As used herein, the term "composition" is intended to encompass a product comprising the specified ingredients in the specified amounts, as well as any product which results, directly or indirectly, from a combination of the specified ingredients in the specified amounts.

The term "stabilizing", as used herein, refers to any process which facilitates and/or enables an active agent to remain in solution. The term "stabilizing", as used herein, also refers to any means or process which inhibits and/or reduces the tendency of a muscarinic agonist, including aceclidine, to degrade.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

The term muscarinic receptor agonist ("muscarinic agonist") encompasses agonists that activate muscarinic acetylcholine receptors ("muscarinic receptors"). Muscarinic receptors are divided into five subtypes named M1-M5. Muscarinic agonists of the present invention include those muscarinic agonists that preferentially activate M1 and M3 receptors over M2, M4 and M5 receptors ("M1/M3 agonists"). M1/M3 agonists include but are not limited to aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxasdiazol-5-yl]-1,4,5,6-tetrahydropyrimidine hydrochloride), N-arylurea-substituted 3-morpholine arecolines, pilocarpine, carbachol, VUO255-035 (N-[3-oxo-3-[4-(4-pyridinyl)-1-piperazinyl]propyl]-2,1,3-benzothiadiazole-4-sulfonamide), benzylquinolone carboxylic acid (BQCA), WAY-132983, AFB267B (NGX267), AC-42, AC-260584, chloropyrazines including but not limited to L-687, 306, L-689-660, 77-LH-28-1, LY593039, and any quinuclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof. Preferred M1/M3 agonists are aceclidine, pilocarpine and carbachol. In a preferred embodiment, muscarinic agonists of the present invention include those muscarinic agonist that preferentially activate M1 and M3 over M2, M4, and M5; and even more preferably activate M1 over M3. In another preferred embodiment muscarinic agonist of the present invention include those muscarinic agonists that only activate M1.

The term "aceclidine" encompasses its salts, esters, analogues, prodrugs and derivatives including, but not limited to, aceclidine as a racemic mixture, aceclidine (R) enantiomer, aceclidine (S) enantiomer, aceclidine analogues, including, but not limited to, highly M1 selective 1,2,5 thiadiazole substituted analogues like those disclosed in Ward. J. S. et al., 1,2,5-Thiadiazole analogues of aceclidine as potent ml muscarinic agonists, *J Med Chem*, 1998, Jan. 29, 41(3), 379-392 and aceclidine prodrugs including but not limited to carbamate esters.

The term "selective α-2 adrenergic receptor agonists" or "α-2 agonist" encompasses all α-2 adrenergic receptor agonists which have a binding affinity of 900-fold or greater for α-2 over α-1 adrenergic receptors, or 300-fold or greater for α-2a or α-2b over α-1 adrenergic receptors. The term also encompasses pharmaceutically acceptable salts, esters, prodrugs, and other derivatives of selective α-2 adrenergic receptor agonists.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, and Alphagan® brimonidine tartrate ophthalmic solution.

The terms "treating" and "treatment" refer to reversing, ameliorating, alleviating, inhibiting, reducing, preventing or slowing the progress of the disease, disorder, or condition to which such terms apply, or one or more symptoms of such disease, disorder, or condition.

The term "pharmaceutically acceptable" describes a material that is not biologically or otherwise undesirable (i.e. without causing an unacceptable level of undesirable biological effects or interacting in a deleterious manner).

As used herein, the term "pharmaceutically effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, a "pharmaceutically effective amount" will depend upon the context in which it is being administered. A pharmaceutically effective amount may be administered in one or more prophylactic or therapeutic administrations.

The term "prodrugs" refers to compounds, including, but not limited to, monomers and dimers of the compounds of the invention, which have cleavable groups and become, under physiological conditions, compounds which are pharmaceutically active in vivo.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

The term "higher order aberrations" refers to aberrations in the visual field selected from starbursts, halos (spherical aberration), double vision, multiple images, smeared vision, coma and trefoil.

The term "cold chain" refers to storage at temperatures from about 2 to about 8° C. from manufacture to immediately prior to administration.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences,* 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, hyaluronic acid, malic acid, sulphuric acid and phosphoric acid and such organic acids as oxalic acid, malic acid, maleic acid, methanosulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, a heteroaryl group or other suitable substituent.

Methods of the Invention

In certain other embodiments, the present invention is directed to methods of treating presbyopia, irregular astigmatism, and/or refractive error, comprising administering a composition comprising from about 0.1% to about 4.0% w/v of a muscarinic agonist and from about 0.07% to about 0.1% w/v brimonidine to a subject in need thereof.

In certain embodiments, the present invention is directed to methods for the treatment of presbyopia comprising administering a composition comprising from about 0.1% to about 4.0% w/v of a muscarinic agonist and from about 0.07% to about 0.15% w/v brimonidine to a subject in need thereof.

In certain embodiments, the present invention is directed to methods for the treatment of myopia comprising administering a composition comprising from about 0.1% to about 4.0% w/v of a muscarinic agonist and from about 0.07% to about 0.15% w/v brimonidine to a subject in need thereof.

In certain preferred embodiments, the present invention is directed to methods for preventing myopia comprising administering a composition comprising administering a composition comprising from about 0.1% to about 4.0% w/v of a muscarinic agonist and from about 0.07% to about 0.15% w/v brimonidine to a subject in need thereof.

In certain other preferred embodiments, the present invention is directed to methods for ameliorating myopia comprising administering a composition comprising administering a composition comprising from about 0.1% to about 4.0% w/v of a muscarinic agonist and from about 0.07% to about 0.15% w/v brimonidine to a subject in need thereof.

In certain other preferred embodiments, the present invention is directed to methods for reducing myopia comprising administering a composition comprising administering a composition comprising from about 0.1% to about 4.0% w/v of a muscarinic agonist and from about 0.07% to about 0.15% w/v brimonidine to a subject in need thereof.

In certain other preferred embodiments, the subject in need of preventing myopia is the offspring of a parent with myopia.

In certain other preferred embodiments, the present invention is directed to a method for treating myopia comprising administering a composition comprising about 1.25% w/v aceclidine, about 0.08% w/v brimonidine, about 1.4% w/v carboxymethyl cellulose to a subject in need thereof, wherein the subject is older than 5 years of age and younger than 35 years of age, preferably the composition has a pH of about 5.75 and further comprises potassium sorbate and about 4 millimolar phosphate buffer, preferably the subject does not experience an increase in accommodation and optionally, the composition further comprises 0.0075% w/v cyclopentolate hydrochloride.

Compositions of the Invention

In one embodiment, the present invention is directed to an ophthalmological composition comprising from about 0.1 to about 4.0% w/v, and from about 0.07% to about 0.15% w/v brimonidine.

In a preferred embodiment, the muscarinic agonist is aceclidine. In a more preferred embodiment, aceclidine is at a concentration from about 0.1% to about 2.0% w/v, more preferably from about 0.2% to about 2.0% w/v and even more preferably from about 0.25% to about 2.0% w/v, even more preferably from about 0.3% to about 2.0% w/v or from about 0.5% to about 2.0% w/v or about 0.75% to about 2.0% w/v or from about 1.0% to about 2.0% w/v and still even more preferably from about 1.65% to about 1.85% w/v, and most preferably about 1.75% w/v. As aceclidine is a tertiary amine with asymmetry, both a + and − optical isomer exists (where in some studies (+) is more potent and in others it is felt (−) may be more potent). For the above concentrations polarimetry demonstrated an exactly equal ratio of (+) and (−) isomer for these concentrations. Altering this ratio could therefore alter this concentration range proportional to a change in ratio.

In another preferred embodiment, the muscarinic agonist is pilocarpine. In a more preferred embodiment, pilocarpine is at a concentration from about 0.3% to about 2% w/v.

In another preferred embodiment, the muscarinic agonist is carbachol. In a more preferred embodiment, carbachol is at a concentration from about 1% to about 4% w/v, even more preferably from about 2% to about 2.75% w/v.

In another preferred embodiment, brimonidine is at a concentration from about 0.07% to about 0.15% w/v, preferably from about 0.07% to about 0.15% w/v, more preferably from about 0.07% to about 0.1% w/v, even more preferably from about 0.07% to about 0.09% w/v and most preferably about 0.075% or about 0.08% w/v.

The present invention is further directed to an ophthalmological composition comprising a muscarinic agonist, brimonidine, a nonionic surfactant above its critical micellar concentration for the composition, and a viscosity enhancing agent; or alternatively an in-situ gelling agent. In preferred embodiments the initial viscosity of the composition on topical application is above 20 cps, preferably above 50 cps, and more preferably at about 65 cps or more at 25° C. and 0 shear.

Nonionic surfactants suitable for the present invention include a polysorbate, tyloxapol, a poloxamer, a cyclodextrin, vitamin E TPGS, a polyoxyl castor oil, a polyoxyl stearate, polyethylene glycol, a polyoxyethylene glycol alkyl ether and 2-[[10,13-dimethyl-17-(6-methylheptan-2-yl)-2,3,4,7,8,9,11,12,14,15,16,17-dodecahydro-1H-cyclopenta[a]phenanthren yl]oxy]ethanol. Preferred embodiments include Poloxamer 80, Poloxamer 188, Poloxamer 407, Polysorbate 20, Polysorbate 80, ionically charged (e.g. anionic) beta-cyclodextrins with or without a butyrated salt (Captisol®) 2-hydroxypropyl beta cyclodextrin ("HPβCD"), alpha cyclodextrins, gamma cyclodextrins, Polyoxyl 35 castor oil, and Polyoxyl 40 hydrogenated castor oil or combinations thereof. Further, substitution of other nonionic surfactants compatible with ophthalmological use allows for similar formulation advantages, which may include but is not limited to one or more of a nonionizing surfactant such as poloxamer, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxyl, polyoxyl stearate, nonoxynol, octoxynol 40, octyphenol ethoxylates, nonyl phenol ethoxylates, capryols, lauroglycol, polyethylene glycol ("PEG"), Brij® 35, 78, 98, 700 (polyoxyethylene glycol alkyl ethers), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris(hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl) methyl-2-aminoethane sulfonic acid (TES), 2-Amino-2-hydroxymethyl-propane-1,3-diol (Tris), tyloxapol, Solulan™ C-24 (2-[[10,13-dimethyl-17-(6-methylheptan yl)-2,3,4,7,8,9,11,12,14,15,16,17-dodecahydro-1H-cyclopenta[a]phenanthren-3-yl] oxy]ethanol) and Span® 20-80 (sorbitan monolaurate, sorbitan monopalmitate, sorbitan monostearate, and sorbitan monooleate). In certain embodiments the addition of an anionic surfactant such as sodium lauryl sulfate and or sodium ester lauryl sulfate may be preferred. In other embodiments the addition of polysorbate 80 is preferred. In addition to the above nonionic surfactants any nonionic surfactant is suitable for use in the present invention as long as the concentration of the nonionic surfactant is such that it is above the critical micellar concentration for that non-ionic surfactant. Preferably, the nonionic surfactants used in the present invention achieve submicron diameter micelles, more preferably less than 200 nanometers and more preferably less than 150 nanometers in diameter.

In a preferred embodiment, the nonionic surfactant is present in compositions of the present invention at a concentration from about 0.1% to about 15% w/v.

Ophthalmological in situ gels which may be substituted for or added in addition to one or more nonionic surfactants include but are not limited to gelatin, carbomers of various molecular weights including carbomer 934 P and 974 P, xanthan gums, alginic acid (alginate), guar gums, locust bean gum, chitosan, pectins and other gelling agents well known to experts in the art.

In preferred embodiments the nonionic surfactant is polyoxyl 40 stearate at a concentration from about 1 to about 15% w/v, more preferably at about 5.5% w/v.

In other preferred embodiments, the nonionic surfactant is polysorbate 80 at a concentration from about 0.5% to about 10% w/v, more preferably from about 1% to about 7% w/v and even more preferably from about 2% to about 5% w/v, yet more preferably from about 2.5% to about 4% w/v and most preferably at about 2.5% or 2.75% or 3% or 4% or 5% w/v.

Viscosity agents suitable for the present invention include, but are not limited to gums such as guar gum, hydroxypropyl-guar ("hp-guar"), and xanthan gum, alginate, chitosan, gelrite, hyaluronic acid, dextran, Carbopol® (polyacrylic acid or carbomer) including Carbopol® 900 series including Carbopol® 940 (carbomer 940), Carbopol® 910 (carbomer 910) and Carbopol® 934 (carbomer 934), cellulose derivatives such as high molecular weight carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxypropylethyl cellulose, and hydroxyethyl cellulose, polyethylene glycol, polyvinyl alcohol, polyvinyl chloride, polyvinyl pyrrolidone, gellan, carrageenan, alginic acid, carboxyvinyl polymer or combinations thereof.

In a preferred embodiment the viscosity agent will provide a viscosity of the total composition from about 50 to about 10,000 cps, more preferably from about 50 to about 5,000 cps, even more preferably from about 100 to about 500 cps, yet more preferably from about 100 to about 200 cps and most preferably from about 120 to about 140 cps at 25° C. and 0 shear.

In another preferred embodiment the viscosity agent will have an equilibration viscosity less than 100 cps, preferably from about 15 to about 35 cps, and most preferably at about 30 cps. In a preferred embodiment the viscosity agent is Carbopol® 940 (polymer gel thickening agent carbomer 940) at a concentration from about 0.05% to about 1.5% w/v, preferably from about 0.09% to about 1.0% w/v, more preferably at 0.09%, 0.25%, 0.5%, 0.75%, 0.9% or 1.0% w/v. In certain combinations it has been surprisingly discovered nonionic surfactant/viscosity combinations may result in phase separation over time with precipitate formation. In such situations, particularly for polyoxyls, in a preferred embodiment polyoxyl 40 stearate, and cellulose derivatives, particularly hydroxypropylmethyl cellulose, use of a nonpolysaccharide derivative for viscosity enhancement, such as polyacrylic acid derivatives (carbomers, carbomer 934 or 940 in preferred embodiments) may prevent such separation; or alternatively use of a non polyoxyl nonionic surfactant, such as polysorbate 80 with either a cellulose derivative or noncellulose derivative viscosity agent may be substituted.

In another preferred embodiment, the viscosity agent is carboxymethyl cellulose at a concentration from about 0.1% to about 2% w/v, more preferably from 0.25% to about 1.4% w/v and yet more preferably from about 1.0% to about 1.40% w/v, yet more preferably from about 1.25% to about 1.40% w/v, when at a viscosity of 3,500 cps at 25° C. in a 2% solution.

In another preferred embodiment, the viscosity agent is hydroxypropylmethyl cellulose at a concentration from about 0.1% to about 2% w/v, more preferably from about 0.5% to about 1.75% w/v, even more preferably about 0.75% or 1.5% w/v, still more preferably from about 1.0% to about 1.5% w/v, even more preferably from about 1.0% to about 1.40% w/v and yet more preferably from about 1.25% to about 1.40% w/v.

Cryoprotectants are compounds that either prevent freezing or prevent damage to compounds during freezing. As used herein, the term "cryoprotectant" or "cryoprotectants" include lyoprotectants. Cryoprotectants suitable for use in the subject invention include, but are not limited to, a polyol, a sugar, an alcohol, a lower alkanol, a lipophilic solvent, a hydrophilic solvent, a bulking agent, a solubilizer, a surfactant, an antioxidant, a cyclodextrin, a maltodextrin, colloidal silicon dioxide, polyvinyl alcohol, glycine, 2-methyl-2,4-pentanediol, cellobiose, gelatin, polyethylene glycol (PEG), dimethyl sulfoxide (DMSO), formamide, antifreeze protein 752 or a combination thereof.

As used herein the term "polyol" refers to compounds with multiple hydroxyl functional groups available for organic reactions such as monomeric polyols such as glycerin, pentaerythritol, ethylene glycol and sucrose. Further, polyols may refer to polymeric polyols including glycerin, pentaerythritol, ethylene glycol and sucrose reacted with propylene oxide or ethylene oxide. In a preferred embodiment, polyols are selected from the group consisting of mannitol, glycerol, erythritol, lactitol, xylitol, sorbitol, isosorbide, ethylene glycol, propylene glycol, maltitol, threitol, arabitol and ribitol. In a more preferred embodiment, the polyol is mannitol.

Sugars suitable for use in the present invention as cryoprotectants include, but are not limited to, glucose, sucrose, trehalose, lactose, maltose, fructose and dextran.

In another preferred embodiment, alcohols include, but are not limited to, methanol.

In one embodiment, the present invention individually excludes each cryoprotectant from the definition of cryoprotectant.

Cryoprotectants may be at present in compositions of the present invention at a concentration from about 0.1% to about 99% w/v, preferably from about 1% to about 50% w/v, more preferably from about 1% to about 10% w/v.

As used herein "lower alkanols" include C1-C6 alkanols. Lower alkanols, suitable for use in the present invention include, but are not limited to, amyl alcohol, butanol, sec-butanol, t-butyl alcohol, n-butyl alcohol, ethanol, isobutanol, methanol. isopropanol and propanol.

Bulking agents suitable for use in the present invention include, but are not limited to, saccharide, polyvinylpyrrolidone, cyclodextrin and trehalose.

Solubilizers suitable for use in the present invention include, but are not limited to, cyclic amide, gentisic acid and cyclodextrins.

In a preferred embodiment, surfactants suitable for use in the present invention include, but are not limited to, nonionic surfactants, more preferably surfactants with a hydrophilic-lipophilic balance ("HLB") value of 1 to 18.

In a preferred embodiment, antioxidants suitable for use in the present invention include, but are not limited to, bisulfite, ascorbic acid, disodium- or tetrasodium ethylenediaminetetraacetic acid, citrate, butylated hydroxyanisole ("BHA"), butylated hydroxytoluene ("BHT"), a sulfoxylate, propyl gallate, an amino acid containing a thio group, and a thiol.

Not wishing to be held to particularly theory, it appears the quinuclidine nucleus of the heterocyclic nitrogen on aceclidine is so electron rich it easily attacks surrounding compounds as well as itself.

It is a discovery of the present invention that several modifications may singly or in combination be used to enhance cold chain stability storage, including in addition to in a preferred embodiment aceclidine 1.40%-1.75%, tropicamide 0.025%-0.10% and optionally a nonionic surfactant such as polyoxyl 40 stearate 0.5%-10%, preferably 5.5% one or more of (See Table 3):

Acidic pH, preferably less than 5.5, preferably less than 5.0 and most preferably at a pH of about 4.75;

Viscosity agent, preferably at 25° C. viscosity of about 15-50 cps, and more preferably 20-45 cps, where a preferred embodiment is carbomer 940 0.09%-1.5%;

Addition of a cryoprotectant, in a preferred embodiment a polyol, preferably Mannitol 2.5%-4.0%;

Addition of a buffer, where acetate or phosphate buffers are preferred, 2-100 mmole range with 3-5 mmole is preferred; and Addition of a preservative, where BAK 0.015% is preferred.

In another preferred embodiment a pH less than physiologic pH is found to enhance the whitening effect for brimonidine and reduce corneal penetration resulting in longer duration of effect, preferably at a pH below about 6.0, more preferably from about pH about 4.5 to about 6.0, and even more preferably at a pH from about 5.0 to about 6.0. However, redness reduction is achieved at all pHs. Enhancement of aceclidine absorption occurs at alkaline pH, such that a stronger effect occurs from a given concentration, and therefore while effective at pH ranges from 4.5 to 8.0, pH range of 6.5 to 7.5 results in a stronger effect.

The present invention is further directed to an ophthalmological composition further comprising a cycloplegic agent. It is a surprising and totally unexpected discovery of the present invention that certain cycloplegic agents can be combined with muscarinic agonist, particularly miotic agents, particularly aceclidine, without reducing miotic onset, magnitude, or duration; and further blunt the normally attendant spike in miotic effect coinciding with time of peak absorption in aqueous formulations to provide a constant miosis versus time after onset from 15 to 30 minutes to 6 to 10 hours depending on the desired formulation. The addition of the cycloplegic agent also reduces any residual associated discomfort that may otherwise occur soon after topical instillation, which presumably is a result of ciliary spasms or excessive pupillary miosis.

Cycloplegic agents suitable for the present invention include, but are not limited to, atropine, Cyclogyl® (cyclopentolate hydrochloride), hyoscine, pirenzepine, tropicamide, atropine, 4-diphenylacetoxy-N-methylpiperidine methobromide (4-DAMP), AF-DX 384, methoctramine, tripitramine, darifenacin, solifenacin (Vesicare), tolterodine, oxybutynin, ipratropium, oxitropium, tiotropium (Spriva), and otenzepad (a.k.a. AF-DX 116 or 11-{[2-(diethylamino)methyl]-1-piperidinyl}acetyl]-5,11-dihydro-6H-pyrido[2,3b][1,4]benzodiazepine-6-one). In a preferred embodiment, the cycloplegic agent may be present in compositions of the present invention at a concentration from about 0.001% to about 0.01% w/v, more preferably at about 0.005% w/v.

In a preferred embodiment the cycloplegic agent is tropicamide at a concentration from about 0.001% to about 0.075% w/v, more preferably from about 0.005% to about 0.015% w/v and still more preferably from about 0.005% to about 0.011% w/v, from about 0.005% to about 0.007% w/v and from about 0.005% to about 0.006% w/v or at about 0.0035% w/v. In another preferred embodiment the cycloplegic agent is a mixture of tropicamide at a concentration from about 0.04% to about 0.07% w/v or pirenzepine or otenzepad at a concentration from about 0.002% to about 0.05% w/v.

In a preferred embodiment, tropicamide 0.01% w/v was found to slightly reduce brow ache, 0.030% w/v to further reduce brow ache and from 0.04% to about 0.07% w/v to completely eliminate brow ache without reduction of the average pupillary miosis diameter over duration of effect. Tropicamide in preferred embodiments has demonstrated completely unexpected sensitivity of effect, where at about 0.04% w/v unexpectedly and very effectively reduces or eliminates brow ache and ciliary spasm pain, becoming very noticeably further reduced at 0.042% w/v and absent at 0.044% w/v in a preferred embodiment with no cycloplegia (surprising due to its common use as a pupil dilating agent). Yet, tropicamide did not reduce the mean degree of pupil miosis, the time of onset of pupil miosis or the subsequent visual benefits. On the contrary, tropicamide blunted the peak miosis seen in aqueous formulations to create a smooth consistent miotic effect over time. It allowed modulation of peak pupil miosis to achieve a more even effect over time with no dilation as has been found with its prior use. Specifically, tropicamide is useful to prevent transient constriction below 1.50 mm at 30 to 60 minutes following aceclidine in some embodiments and to reduce transient excessive and undesirable dimming of vision that may otherwise occur at peak onset of about 30 minutes. As an example, an ophthalmological composition comprising 1.53% w/v aceclidine, 5% w/v HPβCD, 0.75% w/v CMC, 0.25% w/v NaCl, 0.01% w/v BAK and a phosphate buffer at pH 7.0; or 1.45% w/v aceclidine; 5.5% w/v polyoxyl 40 stearate; 0.80% w/v CMC; 0.037% w/v NaCl; 0.015% w/v EDTA; 0.007% w/v BAK and 5 mM phosphate buffer at a pH 7.0; was varied from 0.040% w/v tropicamide, where moderate dimming was noted, to 0.044% w/v tropicamide where dimming became almost undetectable other than in extremely dim light conditions. This additional pupil size modulation with a cycloplegic agent allows aceclidine concentrations sufficient for prolonged effect while blunting the attendant peak excessive constriction that is undesirable as well as any uncomfortable brow ache. Surprisingly and due to its short-acting nature, tropicamide achieves this blunting effect without causing mydriasis. Further, in a preferred embodiment, tropicamide 0.014% w/v was found to reduce brow ache, 0.021% w/v to further reduce brow ache and from 0.028% to 0.060% w/v and in some embodiments up to 0.09% w/v to completely eliminate brow ache without cycloplegia (i.e. paralysis of ciliary muscle of the eye).

It has been found for a racemic 50:50 mixture of (+) and (−) aceclidine optical isomers (where in some studies (+) is more potent and in others it is felt (−) may be more potent) tropicamide effects may vary depending on the ratio of aceclidine to tropicamide. For example, in an ophthalmological composition of the present invention comprising 1.55% w/v aceclidine, 5.5% w/v HPβCD or in a preferred embodiment polyoxyl 40 stearate, 0.75% w/v CMC (1%=2,500 centipoise), 0.25% w/v NaCl, and 0.01% w/v BAK and at pH 7.5, 0.042% w/v tropicamide can be differentiated from even 0.035% w/v, with the former demonstrating normal indoor night vision and the latter slight dimming that becomes more noticeable at still lower concentrations. At higher concentrations, such as from about 0.075% to about 0.090% w/v tropicamide, loss of optimal range pupil constriction 1.50 mm to 1.80 mm range begins, and frank mydriasis at higher concentrations begins to occur. As isomer ratio may alter the effective concentration, this must be factored into the clinical efficacy anticipated using aceclidine; for preferred embodiments of the present invention a polarimeter was used to determine an exact 50:50 isomer ratio was used (personal communication Toronto Research Chemicals).

Figure 2:
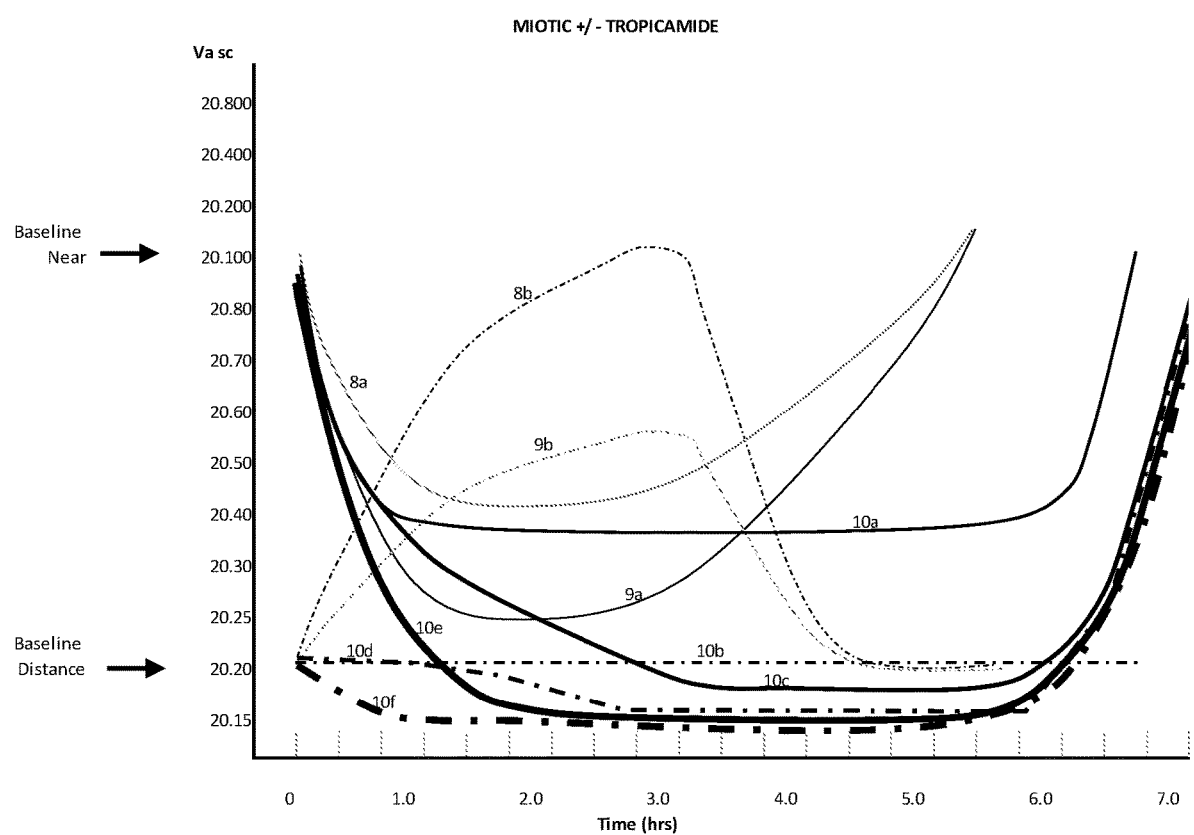
FIG. 2 is a graphical representation of the effects of pilocarpine and aceclidine with or without tropicamide and with or without a carrier on near and distance vision in a patient over the age of 45.

FIG. 2 shows the effect of a miotic agent with or without a cycloplegic agent and with or without a carrier. Subject is an emmetrope over the age of 45 with a baseline near vision of 20.100 and baseline distance vision of 20.20. Topical administration to the eye of 1% w/v pilocarpine in saline solution results in an improvement of near vision to 20.40 (8a), however this improvement comes at the expense of a reduction in distance vision to 20.100 (8b). The addition of 0.015% w/v tropicamide results in an improvement of near vision to 20.25 (9a) and a lessening of the reduction of distance vision to 20.55 (9b), though in certain instances with some induced irregular astigmatism (mildly blotched areas in reading field of vision). Topical administration of 1.55% w/v aceclidine in saline solution results in an improvement of near vision to 20.40 for an extended time period of 6 hrs (10a) without any effect on the baseline distance vision (10b). 10c and 10d show the effects of administering aceclidine in a carrier composed of 5.5% w/v 2-hydroxypropyl beta cyclodextrin, 0.75% w/v CMC (1%=2,500 centipoise), 0.25% w/v NaCl, and 0.01% w/v BAK. As seen in 10c the carrier increases the beneficial effect of aceclidine resulting in better than 20.20 near vision. As seen in 10d a similar increase in distance vision occurs. 10e and 10f show the effects of adding 0.042% w/v tropicamide to the aceclidine in the carrier. As seen in 10e near vision is improved to 20.15 with a quicker onset of maximum visual acuity. As seen in 10f a similar improvement is seen in distance vision. Taken together, FIG. 2 shows that aceclidine is capable of temporarily correcting near vision in a presbyopic subject without affecting the baseline distance vision. Similar results can be achieved with a different miotic agent, pilocarpine, with the addition of a cycloplegic agent such as tropicamide. A proper drug carrier can also have a beneficial effect.

The present invention is further directed to an ophthalmological composition further comprising a tonicity adjustor and a preservative.

A tonicity adjustor can be, without limitation, a salt such as sodium chloride ("NaCl"), potassium chloride, mannitol or glycerin, or another pharmaceutically or ophthalmologically acceptable tonicity adjustor.

Preservatives that can be used with the present invention include, but are not limited to, benzalkonium chloride ("BAK"), sorbic acid, oxychloro complex, citric acid, chlorobutanol, thimerosal, phenylmercuric acetate, disodium ethylenediaminetetraacetic acid, phenylmercuric nitrate, perborate or benzyl alcohol. In a preferred embodiment the preservative is BAK, sorbic acid, oxychloro complex or a combination thereof. In a yet more preferred embodiment BAK is at a concentration of about 0.001% to about 1.0% w/v, more preferably at a concentration of about 0.007%, 0.01% or 0.02% w/v. In another preferred embodiment the preservative is perborate at a concentration of 0.01% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, phosphate buffers and borate buffers. It is understood that acids or bases can be used to adjust the pH of the composition as needed, preferably of 1 to 10 mM concentration, and more preferably about 3 mM or 5 mM. In another preferred embodiment, buffers may be present in compositions of the present invention at a concentration from about 0.01% to about 1% w/v, more preferably from about 0.05% to about 0.5% w/v and even more preferably from about 0.06% to about 0.1% and even more preferably at about 0.06%, 0.08% or 0.1% w/v. In a preferred embodiment the pH is from about 4.0 to about 8.0, in a more preferred embodiment the pH is about 6.5 or less or about 6.0 or less below. In a more preferred embodiment, the pH is from about 5.0 to about 5.75 and even more preferably about 5.0, about 5.5, about 5.75 or about 6.0.

The present invention is further directed to an ophthalmological composition further comprising an antioxidant. Antioxidants that can be used with the present invention include but are not limited to disodium ethylenediaminetetraacetic acid at a concentration from about 0.005% to about 0.50% w/v, citrate at a concentration from about 0.01% to about 0.3% w/w, dicalcium diethylenetriamine pentaacetic acid ("Ca2DTPA") at a concentration from about 0.001% to about 0.2% w/v, preferably about 0.01% w/v Ca2DTPA which can be formulated by adding 0.0084% w/v $Ca(OH)_2$ and 0.0032% w/v pentetic acid to the formulation and mixing slowly. Further combinations of antioxidants can be used. Other antioxidants that can be used with the present invention include those well known to experts in the art such as ethylenediaminetetraacetic acid at a concentration from about 0.0001% to about 0.015% w/v.

The following representative embodiments are provided solely for illustrative purposes and are not meant to limit the invention in any way.

Representative Embodiments

In one embodiment, the ophthalmological composition comprises:
aceclidine at a concentration of about 1.75% w/v; and
mannitol at a concentration of about 2.5% w/v.

In another embodiment, the ophthalmological composition comprises:
aceclidine at a concentration of about 1.75% w/v;
mannitol at a concentration of about 2.5% w/v; and
tropicamide at a concentration of about 0.02% w/v.

In another embodiment, the ophthalmological composition comprises:
aceclidine at a concentration of about 1.75% w/v;
mannitol at a concentration of about 2.5% w/v;
polysorbate 80 at a concentration of about 5.0% w/v;
carboxymethyl cellulose at a concentration of about 1.4% w/v;
BAK at a concentration of about 0.015% w/v; and
phosphate buffer at a concentration of about 3 mM, wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.5% w/v;
NaCl at a concentration from about 0.10% to about 0.50% w/v;
Carbopol® 940 polymer gel thickening agent at a concentration of about 0.95% w/v;
BAK at a concentration of about 0.01% w/v; and
phosphate buffer at a concentration of about 3 mM, wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 2.0% w/v;
NaCl at a concentration of about 0.50% w/v
Carbopol® 940 polymer gel thickening agent at a concentration of about 1.5% w/v;
BAK at a concentration of about 0.015% w/v; and
phosphate buffer at a concentration of about 3 mM,
wherein the pH is about 5.25.

In another embodiment, the ophthalmological composition comprises:
aceclidine at a concentration of about 1.75% w/v;
mannitol at a concentration of about 2.5% w/v;
polysorbate 80 at a concentration of about 0.25% w/v;
NaCl at a concentration of about 0.1% w/v;
boric acid at a concentration of about 0.12% w/v;
Carbopol® 940 polymer gel thickening agent at a concentration of about 0.95% w/v; and
BAK at a concentration of about 0.015% w/v;
wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.50% w/v;
NaCl at a concentration of about 0.05% w/v;
boric acid at a concentration of about 0.2% w/v;
Carbopol® 940 polymer gel thickening agent at a concentration of about 0.95% w/v;
BAK at a concentration of about 0.01% w/v; and
phosphate buffer at a concentration of about 3 mM,
wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.1% w/v;
boric acid at a concentration of about 0.2% w/v;
Carbopol® 940 polymer gel thickening agent at a concentration of about 0.9% w/v;
BAK at a concentration of about 0.05% w/v; and
phosphate buffer at a concentration of about 3 mM,
wherein the pH is about 5.

In another embodiment, the ophthalmological composition comprises:
aceclidine at a concentration of about 1.75% w/v;
mannitol at a concentration of about 2.5% w/v;
polysorbate 80 at a concentration of about 0.1% w/v;
NaCl at a concentration of about 0.1% w/v;
boric acid at a concentration of about 0.12% w/v;
Carbopol® 940 polymer gel thickening agent at a concentration of about 0.95% w/v;
BAK at a concentration of about 0.01% w/v; and
phosphate buffer at a concentration of about 3 mM,
wherein the pH is about 5.

In another embodiment, the ophthalmological composition comprises:
aceclidine at a concentration of about 1.75% w/v;
tropicamide at a concentration of about 0.01% w/v;
mannitol at a concentration of about 2.5% w/v;
polysorbate 80 at a concentration of about 5.0% w/v;
CMC at a concentration of about 1.4% w/v;
BAK at a concentration of about 0.015% w/v; and
phosphate buffer at a concentration of about 3 mM,
wherein the pH is about 5.

In another embodiment, the ophthalmological composition comprises:
aceclidine at a concentration of about 1.75% w/v;
tropicamide at a concentration of about 0.02% w/v;
mannitol at a concentration of about 2.5% w/v;
polysorbate 80 at a concentration of about 0.25% w/v;
NaCl at a concentration of about 0.1% w/v;
boric acid at a concentration of about 0.12% w/v;
Carbopol® 940 polymer gel thickening agent at a concentration of about 0.95% w/v; and
BAK at a concentration of about 0.01% w/v.
wherein the pH is about 5.

In another embodiment, the ophthalmological composition comprises:
aceclidine at a concentration of about 1.75% w/v;
tropicamide at a concentration of about 0.015% w/v;
mannitol at a concentration of about 2.5% w/v;
polysorbate 80 at a concentration of about 0.75% w/v;
NaCl at a concentration of about 0.05% w/v;
boric acid at a concentration of about 0.2% w/v;
Carbopol® 940 polymer gel thickening agent at a concentration of about 0.95% w/v;
BAK at a concentration of about 0.01% w/v; and
phosphate buffer at a concentration of about 3 mM.
wherein the pH is about 5.

In another embodiment, the ophthalmological composition comprises:
aceclidine at a concentration of about 1.75% w/v;
tropicamide at a concentration of about 0.025% w/v;
mannitol at a concentration of about 2.5% w/v;
polysorbate 80 at a concentration of about 0.1% w/v;
boric acid at a concentration of about 0.2% w/v;
Carbopol® 940 polymer gel thickening agent at a concentration of about 0.9% w/v;
BAK at a concentration of about 0.05% w/v; and
phosphate buffer at a concentration of about 3 mM.
wherein the pH is about 5.

In another embodiment, the ophthalmological composition comprises:
aceclidine at a concentration of about 1.75% w/v;
tropicamide at a concentration of about 0.02% w/v;
mannitol at a concentration of about 2.5% w/v;
polysorbate 80 at a concentration of about 0.1% w/v;
NaCl at a concentration of about 0.1% w/v;
boric acid at a concentration of about 0.12% w/v;
Carbopol® 940 polymer gel thickening agent at a concentration of about 0.95% w/v;
BAK at a concentration of about 0.01% w/v; and
phosphate buffer at a concentration of about 3 mM.
wherein the pH is about 5.

In another embodiment, the ophthalmological composition comprises:
aceclidine at a concentration of about 1.75% w/v;
tropicamide at a concentration of about 0.040% w/v;
polyoxyl 40 stearate at a concentration of about 5.0% w/v;
mannitol at a concentration of about 2.5% w/v;
acetate or phosphate buffer at a concentration of about 3.0 mM; and
BAK at a concentration of about 0.01% w/v,
wherein said composition has a pH of about 4.75.

In another embodiment, the ophthalmological composition comprises:
aceclidine at a concentration of about 1.55% w/v;
tropicamide at a concentration of about 0.040% w/v;
polyoxyl 40 stearate at a concentration of about 5.0% w/v;
citric acid monohydrate at a concentration of about 0.1% w/v;

mannitol at a concentration of about 4.0% w/v;
Carbopol® 940 polymer gel thickening agent at a concentration of 0.09% w/v; and
acetate or phosphate buffer at a concentration of about 3.0 mM;
wherein said composition has a pH of about 5.0.

In another embodiment, the ophthalmological composition comprises:
aceclidine at a concentration of about 1.50% w/v;
tropicamide at a concentration of about 0.042% w/v;
polyoxyl 40 stearate at a concentration of about 5.5% w/v;
mannitol at a concentration of about 2.5% w/v;
phosphate buffer at a concentration of about 3.0 mM;
Carbopol® 940 polymer gel thickening agent at a concentration of about 0.85% w/v; and
BAK at a concentration of about 0.01% w/v,
wherein said composition has a pH of about 4.75.

In another embodiment, the ophthalmological composition comprises:
aceclidine at a concentration of about 1.45% w/v;
tropicamide at a concentration of about 0.042% w/v;
polyoxyl 40 stearate at a concentration of about 5.5% w/v;
citric acid monohydrate at a concentration of about 0.1% w/v;
acetate buffer at a concentration of about 3.0 mM; and
Carbopol® 940 polymer gel thickening agent at a concentration of about 0.75% w/v,
wherein said composition has a pH of about 4.75.

In another embodiment, the ophthalmological composition comprises:
aceclidine at a concentration of about 1.45% w/v;
tropicamide at a concentration of about 0.042% w/v;
polyoxyl 40 stearate at a concentration of about 5.5% w/v;
mannitol at a concentration of about 2.0% w/v;
citric acid monohydrate at a concentration of about 0.1% w/v;
phosphate buffer at a concentration of about 3.0 mM; and
Carbopol® 940 polymer gel thickening agent at a concentration of about 1.0% w/v,
wherein said composition has a pH of about 4.75.

In another embodiment, the ophthalmological composition comprises:
about 1.75% w/v aceclidine;
about 2.5% w/v mannitol;
about 2.75% w/v polysorbate 80; and
about 1.25%; 1.0%-1.80% w/v hydroxypropylmethyl cellulose (depending on its molecular weight).

In another embodiment, the ophthalmological composition comprises:
about 1.75% w/v aceclidine;
about 0.005% to about 0.011% tropicamide;
about 2.5% w/v mannitol;
about 2.75% w/v polysorbate 80; and
about 1.25%; 1.0%-1.80% w/v hydroxypropylmethyl cellulose (depending on its molecular weight).

In another embodiment, the ophthalmological composition comprises:
about 1.75% w/v aceclidine;
about 0.010% w/v tropicamide;
about 2.5% w/v mannitol;
about 5.0% w/v polysorbate 80;
about 1.40% w/v carboxymethyl cellulose high viscosity;
about 3 mM phosphate buffer; and
about 0.010% BAK=as preservative,
with a pH of about 5.0.

In another embodiment, the ophthalmological composition comprises:
about 1.75% w/v aceclidine;
about 0.006% w/v tropicamide;
about 2.5% w/v mannitol;
about 2.5% w/v polysorbate 80;
about 1.25%; 1.0%-1.80% w/v hydroxypropylmethyl cellulose (depending on its molecular weight);
about 3 mM phosphate buffer; and
about 0.020% BAK=as preservative,
with a pH of about 5.0.

In another embodiment, the ophthalmological composition comprises:
about 1.75% w/v aceclidine;
about 0.006% w/v tropicamide;
about 2.5% w/v mannitol;
about 2.5% w/v polysorbate 80;
about 1.25%; 1.0%-1.80% w/v hydroxypropylmethyl cellulose (depending on its molecular weight);
about 3 mM phosphate buffer;
about 0.50% w/v NaCl; and
about 0.020% BAK=as preservative,
with a pH of about 5.0.

In another embodiment, the ophthalmological composition comprises:
about 1.75% w/v aceclidine;
about 2.5% w/v mannitol;
about 3.5% w/v polysorbate 80;
about 1.25%; 1.0%-1.80% w/v hydroxypropylmethyl cellulose (depending on its molecular weight);
about 3 mM phosphate buffer;
about 0.50% w/v NaCl; and
about 0.020% BAK or 0.15% sorbic acid as preservative,
with a pH of about 5.0.

In another embodiment, the ophthalmological composition comprises:
about 1.75% w/v aceclidine;
about 2.5% w/v mannitol;
about 3.5% w/v polysorbate 80; and
about 1.25%; 1.0%-1.80% w/v hydroxypropylmethyl cellulose (depending on its molecular weight);

In another embodiment, the ophthalmological composition comprises:
about 1.75% w/v aceclidine;
about 2.5% w/v mannitol;
about 3.5% w/v polysorbate 80;
about 1.25%; 1.0%-1.80% w/v hydroxypropylmethyl cellulose (depending on its molecular weight); and
one or more excipient selected from the group consisting of about 0.50% w/v sodium chloride, about 0.02% w/v benzalkonium chloride, about 0.10% w/v sorbate, about 0.01% w/v ethylenediaminetetraacetic acid (EDTA) and 0.10% w/v citric acid.

In another embodiment, the ophthalmological composition comprises:
about 1.75% w/v aceclidine;
about 2.5% w/v mannitol;
about 0.01% w/v tropicamide;
about 0.1% w/v sodium citrate, anhydrous;
about 0.02% w/v benzalkonium chloride;
about 0.12% w/v sorbic acid;
about 0.1% w/v disodium edetate dihydrate;
about 4.0% w/v polysorbate 80; and
about 1.25% w/v hydroxypropylmethyl cellulose,
wherein the pH is about 5.0.

In another embodiment, the ophthalmological composition comprises:
about 1.75% w/v aceclidine;
about 2.5% w/v mannitol;
about 0.01% w/v tropicamide;
about 0.1% w/v sodium citrate, anhydrous;
about 0.02% w/v benzalkonium chloride;
about 0.1% w/v sorbic acid;
about 0.1% w/v EDTA;
about 3.5% w/v polysorbate 80; and
about 1.25%; 1.0%-2.25% w/v hydroxypropylmethyl cellulose (depending on its molecular weight),
wherein the pH is about 5.0.

In another embodiment, the ophthalmological composition comprises:
about 1.75% w/v aceclidine;
about 2.5% w/v mannitol;
about 0.01% w/v tropicamide;
about 3 mM phosphate buffer;
about 0.02% w/v benzalkonium chloride;
about 0.1% w/v sorbic acid;
about 0.1% w/v citrate;
about 3.5% w/v polysorbate 80; and
about 1.25%; 0.25%-2.25% w/v hydroxypropylmethyl cellulose (depending on its molecular weight);
wherein the pH is about 5.0.

In another embodiment, the ophthalmological composition comprises about 1.25% w/v aceclidine, about 0.08% w/v brimonidine, about 2.5% w/v polysorbate, about 1.45% w/v carboxymethyl cellulose, about 0.07% EDTA and about 0.01% w/v potassium sorbate.

In another embodiment, the ophthalmological composition comprises:
aceclidine at a concentration of 1.5% w/v, mannitol at a concentration of 2.5% w/v.

In another embodiment, the ophthalmological composition comprises:
aceclidine at a concentration of 1.55% w/v, mannitol at a concentration of 2.5% w/v.

In another embodiment, the ophthalmological composition comprises:
aceclidine at a concentration of 1.6% w/v, mannitol at a concentration of 2.5% w/v.

In another embodiment, the ophthalmological composition comprises:
aceclidine at a concentration of 1.65% w/v, mannitol at a concentration of 2.5% w/v.

In another embodiment, the ophthalmological composition comprises:
aceclidine at a concentration of 1.7% w/v, mannitol at a concentration of 2.5% w/v.

In another embodiment, the ophthalmological composition comprises:
aceclidine at a concentration of 1.75% w/v, mannitol at a concentration of 2.5% w/v.

In another embodiment, the ophthalmological composition comprises:
aceclidine at a concentration of 1.80% w/v, mannitol at a concentration of 2.75% w/v and Carbopol® 940 polymer gel thickening agent at a concentration of 0.09% w/v.

In another embodiment, the ophthalmological composition comprises:
aceclidine at a concentration of 1.48% w/v, mannitol at a concentration of 1.5% w/v and Carbopol® 940 polymer gel thickening agent at a concentration of 0.50% w/v.

In another embodiment, the ophthalmological composition comprises:
aceclidine at a concentration of 1.80% w/v, mannitol at a concentration of 2.5% w/v and Carbopol® 940 polymer gel thickening agent at a concentration of 0.9% w/v.

In another embodiment, the ophthalmological composition comprises:
about 1.75% w/v aceclidine:
about 0.08% w/v brimonidine;
about 4.0% w/v polysorbate 80; and
about 1.25% w/v hydroxypropylmethyl cellulose,
wherein the composition optionally has a pH from about 5.0 to about 6.0.

In another embodiment, the ophthalmological composition comprises:
about 1.75% w/v aceclidine:
about 0.08% w/v brimonidine;
about 4.0% w/v polysorbate 80;
about 1.25% w/v hydroxypropylmethyl cellulose;
about 0.1% w/v disodium edetate dihydrate; and
from about 0.08% to about 0.1% sodium citrate anhydrous,
wherein the composition optionally has a pH from about 5.0 to about 6.0.

In another embodiment the ophthalmological compositions are any of the following Tables.

TABLE 1

Representative Aceclidine Compositions

| Formula | A | B | C | D | E | F | G | H | I |
|---|---|---|---|---|---|---|---|---|---|
| Aceclidine | 1.75% | 1.35% | 1.40% | 2.40% | 1.50% | 1.00% | 0.75% | 0.55% | 1.50% |
| Polysorbate 80 | — | 1.00% | — | 2.00% | 1.00% | 0.25% | 4.00% | 4.00% | — |
| Poloxamer 407 | — | — | — | — | 0.10% | 1.00% | — | — | — |
| Pol oxamer 188 | — | — | — | 2.00% | 0.10% | 0.25% | — | — | 1.00% |
| Cyclodextrin | — | — | 1.00% | — | 0.50% | 0.25% | — | 1.00% | 1.00% |
| CMC (2% = 3500 cps) | — | — | 0.75% | 0.85% | 1.00% | 0.80% | 1.10% | 1.20% | 0.25% |
| NaCl | 0.90% | 0.80% | 0.90% | 0.75% | 0.75% | 0.85% | 0.90% | 0.90% | 0.90% |
| K Sorbate | 0.10% | 0.10% | 0.10% | 0.12% | 0.12% | 0.10% | 0.10% | 0.10% | 0.10% |

TABLE 2

Representative Aceclidine Compositions

| Formula | J | K | L |
|---|---|---|---|
| Aceclidine | 1.75% | 1.75% | 1.75% |
| Tropicamide | 0.010% | 0.010% | 0.006% |
| Mannitol | — | 2.00% | 2.50% |
| Polysorbate 80 | 1.00% | 2.00% | 4.00% |
| Poloxamer 407 | 0.50% | 0.20% | — |
| Poloxamer 188 | — | 0.20% | — |

TABLE 2-continued

Representative Aceclidine Compositions

| Formula | J | K | L |
|---|---|---|---|
| Cyclodextrin | — | 0.20% | — |
| CMC (2% = 3500 cps) | 1.00% | 0.85% | 1.30% |
| NaCl | 0.90% | 0.65% | 0.90% |
| K Sorbate | 0.10% | 0.10% | 0.10% |

The following Examples are provided solely for illustrative purposes and are not meant to limit the invention in any way.

EXAMPLES

Example 1 Effect of Aceclidine on Vision of Subjects Aged 47 to 67 Years

Table 3 demonstrates the effect on the near focus ability of presbyopic subjects before and after ophthalmological administration of a composition containing aceclidine. Each composition included aceclidine in the concentrations indicated and 5.5% w/v HPβCD, 0.75% w/v CMC, 0.25% w/v NaCl and 0.01% w/v BAK. Additionally, compositions administered to subjects 4 and 5 included 0.125% w/v tropicamide. As aceclidine is an enantiomer, the clinical effectiveness may vary with different ratios. For the present studies a nearly exact 50:50 ratio of stereoisomers was measured as best determined by polarimetry.

TABLE 3

Effects of aceclidine on vision of presbyopic patients.

| | | | | Vision Baseline | | | | Post Gtt 15" | | | | |
|---|---|---|---|---|---|---|---|---|---|---|---|---|
| Date | # | Age | Aceclidine % | R Pre Dist | L Pre Dist | R Pre Near | L Pre Near | R Post Dist | L Post Dist | R Post Near | L Post Near | Effect (h) |
| Aug. 21, 2013 | 1 | 67 | 1.5 | 20.20 | 20.30 | 20.60 | 20.60 | 20.20 | 20.20 | 20.15 | 20.15 | 9.00 |
| Aug. 22, 2013 | 2 | 52 | 1.5 | 20.30 | 20.30 | 20.50 | 20.50 | 20.25 | 20.25 | 20.25 | 20.20 | 8.00 |
| Aug. 23, 2013 | 3 | 61 | 1.5 | 20.40 | 20.30 | 20.60 | 20.50 | 20.20 | 20.25 | 20.15 | 20.15 | 8.00 |
| Aug. 23, 2013 | 4 | 61 | 1.1 | 20.20 | 20.25 | 20.80 | 20.50 | 20.15 | 20.15 | 20.20 | 20.15 | 12.00 |
| Aug. 23, 2013 | 5 | 53 | 1.1 | 20.20 | 20.20 | 20.60 | 20.60 | 20.20 | 20.20 | 20.25 | 20.25 | 7.00 |
| Aug. 24, 2013 | 6 | 47 | 1.5 | 20.25 | 20.25 | 20.100 | 20.100 | 20.20 | 20.20 | 20.15 | 20.15 | 8.00 |
| Aug. 25, 2013 | 7 | 58 | 1.5 | 20.30 | 20.200 | 20.100 | 20.30 | 20.25 | 20.30 | 20.20 | 20.30 | 8.00 |

As seen in Table 3 all subjects had less than perfect near vision (20.20) in both the left and right eye (object at 15 inches from the eye) and most subjects had less than perfect distance vision before administration of the composition. After administration of the composition all subjects experienced an improvement in their near vision that lasted from 7 to 12 hours. Surprisingly, the majority of subjects also experienced improvement of their distance vision for the same time period. Still more surprisingly the improvement in near point was much closer than 16" typically required for comfortable reading, in some cases to about 8.5" more commonly seen in individuals 30 or less. The addition of tropicamide, a cycloplegic agent, had no additive or deleterious effect on vision correction.

Example 2 Modulation of Aceclidine Concentrations in a Preferred Embodiment

Preferred Embodiment

Aceclidine 1.35%-1.55% w/v;
Polyoxyl 40 stearate 5.5% w/v;
NaCl 0.037% w/v;
a viscosity agent, preferably CMC 0.80% w/v or an amount of Carbopol® 934 or 940 polymer gel thickening agent sufficient to achieve a viscosity of from about 5 to about 35 cps upon topical instillation, such as Carbopol® 940 polymer gel thickening agent at a concentration from about 0.09% to about 1.0% w/v;
BAK 0.015% w/v; and
a phosphate, citrate, citrophosphate, or acetate buffer from about 3 to about 10 mM,
wherein the pH is from about 4.75 to about 6.0.
  For 1.35% w/v aceclidine—
    Stinging on topical instillation 0.25/4.0 (lasting about 2-5 seconds);
    Induced redness at 10 minutes: 1.0 to 1.5/4.0;
    Induced redness at 30 minutes: 0.0 to 0.25/4.0;
    Comfort: very high.
    Wetting: very high, the eye maintaining sensation of improved wetting for most of a 24-hour period after a single topical instillation.
    Depth of Focus distance: excellent.
    Depth of Focus near: excellent.

In testing the above formulations on several subjects, it was discovered that there is a slight range in clinical effect depending on the concentration of aceclidine, where 1.35%-1.55% w/v aceclidine is preferred, but for which 1.35% w/v and 1.45% w/v confer the desired benefits on most subjects.

Further, it is discovered that the clinical effect of 1.35% w/v aceclidine can be improved when instilled as follows:
1) baseline effect: 1 drop to each eye.
2) enhanced effect: 2 drops to each eye.
3) greater effect: after 2) above repeat 1) above.
4) maximum effect: after 2) above repeat 2) above.

Example 3 Use of a Preferred Embodiment to Prolong Contact Lens Wear

Preferred Embodiment

Aceclidine 1.45% w/v;
Polyoxyl 40 stearate 5.5% w/v;
NaCl 0.037% w/v;
a viscosity agent, preferably CMC 0.80% w/v or an amount of Carbopol® 934 or 940 polymer gel thickening agent sufficient to achieve a viscosity of from about 5 to about 35 cps upon topical instillation, such as Carbopol® 940 polymer gel thickening agent at a concentration from about 0.09% to about 1.0% w/v;
BAK 0.02% w/v; and
a phosphate, citrate, citrophosphate, or acetate buffer from about 3 to about 10 mM,
wherein the pH is from about 4.75 to about 6.0.

As a baseline, the subject, who normally wore extended wear lenses (Air Optix® contact lenses; Air Optix is a registered trademark of Novartis AG) for daily wear only, slept in these lenses overnight. On arising each morning, the subject's vision was blurred, and the contact lenses required removal and cleaning of film and deposits that had formed overnight. Average vision on arising at distance: 20.60; average vision at near on a Michelson contrast acuity chart: 20.80.

Then, for seven consecutive days the above formulation was instilled between 7 am and 10 am each day as a single dose. Subject wore the Air Optix® contact lenses throughout each day and slept in the lenses overnight. Upon arising each morning, the subject's vision at distance: 20.20+; vision at near 20.40 unaided (consistent with subject's baseline presbyopia when the subject did not wear the lenses overnight and instead inserted the lenses upon arising).

Example 4 Comparison of Effects of Polyoxyl 40 Stearate and Captisol® (Sulfobutylether β-Cyclodextrin

TABLE 4

Comparison of Effects of Polyoxyl 40 Stearate and Captisol ® (sulfobutylether β-cyclodextrin).

|  | #25 | #26 | #27 | #28 | #29 | #30 | #31 | #32 | #33 |
|---|---|---|---|---|---|---|---|---|---|
| Aceclidine | 1.35% | 1.35% | 1.35% | 1.35% | 1.35% | 1.35% | 135% | 1.35% | 1.35% |
| Tropicamide | 0.044% | 0.044% | 0.044% | 0.044% | 0.044% | 0.044% | 0.044% | 0.044% | 0.044% |
| Polyoxyl 40 stearate | 5.5% | 5.5% | 5.5% | 5.5% | 5.5% | 5.5% | 5.5% |  |  |
| Captisol ® |  |  |  |  |  |  |  | 5.5% | 5.5% |
| Cocamidopropyl betaine |  |  |  |  |  |  | 0.10% |  |  |
| EDTA |  |  | 0.015% | 0.015% | 0.005% | 0.005% | 0.005% | 0.005% | 0.015% |
| CMC 1% = 2,500 cps | 0.80% | 0.80% | 0.80% | 0.80% | 0.80% | 0.80% | 0.80% | 0.80% | 0.80% |
| NaCl | 0.037% | 0.037% | 0.037% | 0.037% | 0.037% | 0.037% | 0.037% | 0.037% | 0.037% |
| Mannitol |  |  |  |  |  |  |  | 4% | 4% |
| BAK | 0.007% | 0.007% | 0.007% | 0.007% | 0.007% | 0.007% | 0.007% | 0.007% | 0.007% |
| Borate buffer (mM) | 4 |  | 4 |  | 4 | 4 | 4 | 4 | 4 |
| Phosphate buffer (mM) |  | 4 |  | 4 |  |  |  |  |  |
| pH | 7 | 7 | 7 | 7 | 7 | 7 | 7 | 7 | 7 |
| Redness, 10 min | 1.25 | 1.25 | 2 | 2 | 1.75 | 1.75 | 0 | 0 | 0 |
| Redness, 30 min | 0 | 0 | 1.5 | 1.5 | 1.25 | 1.25 | 0 | 0 | 0 |
| Pupil 30 min (mm) | <2 | <2 | <2 | <2 | <2 | <2 | <2 | <2 | <3 |
| Blur on instill (sec) | 10 | 10 | 10 | 10 | 10 | 10 | 10 | 10 | 10 |
| Ache | 0 | 0 | 0 | 0 | 0 | 0 | 1 | 0 | 0 |
| Rating | 4.00 | 4.00 | 2.00 | 2.00 | 2.50 | 2.50 | 1.00 | 5.00 | TBD |

As seen in Table 4, when using polyoxyl 40 stearate as the surfactant the exclusion of EDTA results in reduced redness and best overall rating among polyoxyl 40 stearate compositions (Formulas #25 and #26). The addition of cocamidopropyl betaine ("CAPB") further reduces redness however results in significant ache (Formula #31). Replacing polyoxyl 40 stearate with Captisol® (sulfobutylether β-cyclodextrin) and adding mannitol achieves similar results in redness reduction as the addition of CAPB to polyoxyl 40 stearate but without the attendant ache resulting in the highest overall rating among aceclidine compositions (Formula #32). After several weeks formulations with Captisol® (sulfobutylether β-cyclodextrin) had an orange hue, possibly indicative of oxidation.

Example 5 Preferred Cold Chain Composition

Composition
aceclidine at a concentration of about 1.40%-1.80% w/v; and
tropicamide at about 0.42% w/v;
polyoxyl 40 stearate at about 5.5% w/v;
mannitol at a concentration of about 2.5% to 4.5% w/v;
carbomer 940 at a concentration of about 0.09% to about 2.0% w/v;
optionally, a preservative such as BAK at a concentration of about 0.2% w/v;
optionally citrate at a concentration of about 0.1%;
optionally with acetate or phosphate buffer at 2-100 mM, more preferably 3-5 mM
wherein said composition has a pH of about 4.50 to about 5.0; and preferably, about 4.75 to about 5.0; and
wherein w/v denotes weight by volume A composition as described above was administered to a 62-year-old subject. It resulted in pupils of 1.8-1.9 mm ou, 20.20+ reading vision, and 20.20+ distance vision; whereas without carbomer 940 reduced effectiveness resulted at 2.5% mannitol, and no near vision effect resulted at 4.0% mannitol. No ciliary spasm or loss of distance vision resulted. Onset was within about 15 minutes. Transient redness of about 1+/out of 4 was noted for about 20 minutes without alpha agonist vasoconstrictor. The presence or absence of BAK had no clinical effect, and was used to provide an optional preservative.

Example 6 Stabile Aceclidine Formulations

Composition Tested:
aceclidine at a concentration of about 1.50% w/v;
tropicamide at a concentration of about 0.042% w/v;
polyoxyl 40 stearate at a concentration of about 5.5% w/v;

mannitol at a concentration of about 2.5% w/v;
citrate at a concentration of about 3 mM;
wherein said composition has a pH of about 4.75.

20 samples of the above composition were divided evenly and stored at 25° C. and 4° C. Prior to storage, initial concentrations of aceclidine were measured using high-pass liquid chromatography ("HPLC"). The amount of aceclidine in each solution was calculated by the area under the principal peak compared to a reference solution of aceclidine. Samples were then subject to storage for 3 months. Aceclidine measurements were taken at 1, 2 and 3 months. Results of the stability test are shown in Table 5.

TABLE 5

Stability of Aceclidine in Cold Chain Storage

|  | 25° C. | 4° C. |
| --- | --- | --- |
| Initial | 100% | 100% |
| 1 month | 92% | 93% |
| 2 months | 75% | 92% |
| 3 months | 50% | 88% |

As seen in Table 5 "cold chain storage" or storage of the aceclidine composition at from 2° C. to 8° C. resulted in a significant increase in stability of aceclidine at all 3 time points.

Example 7 Use of Compositions Containing Little or No Cycloplegic Agent

Aceclidine alone causes incidence migraine-like severe ciliary spasm (brow ache) and myopic blur. These effects are inversely correlated to age with subjects age 40 reporting the highest incidence and subject age 60+ reporting the lowest incidence. The addition of a cycloplegic agent reduces ciliary spasms and attendant brow ache, migranious headache, squeezing pressure around eyes or other symptoms of ciliary spasms. The addition of the cycloplegic agent, surprisingly, does not reduce the myopic effect of aceclidine. The addition of 2.5% w/v mannitol however does reduce the myopic effect of aceclidine. Increasing the aceclidine concentration overcomes this reduction in myopic effect seen with the addition of mannitol. Surprisingly, however, the increase in aceclidine is not coincident with an increase in ciliary spasm. Even more surprising, the concentration of the cycloplegic agent can be reduced or even eliminated in the presence of mannitol without an increase in ciliary spasm. Thus, combining a higher concentration of aceclidine with little to no cycloplegic agent in the presence of mannitol results in an improvement of near vision acuity without attendant side effects on par with lower concentrations of aceclidine and higher concentrations of the cycloplegic agent in the absence of a cycloplegic agent.

Further and unexpectedly, the addition of a nonionic surfactant increases both the quantitative measure of near vision improvement and the duration. This effect is concentration sensitive. In a preferred embodiment the non-ionic surfactant is at least 1%, preferably at least 2%, more preferably from about 1% to about 5%, and most preferably about 5%. For example, polysorbate 80 or polyoxyl 40 stearate at a concentration from about 1% to about 5% w/v results in about 1.5 to about 2.0 lines of improvement and a duration from about 4 to about 5 hours.

Not to be held to particular theory, the increase in concentration of a surfactant may crowd the surface of the cornea, and at an optimal concentration this crowding result in small and probably nanometer diameters, which given the dual polarity of surfactants, where nonionic are most preferred, enhances corneal absorption of the entrapped highly polar aceclidine molecules.

Figure 3:
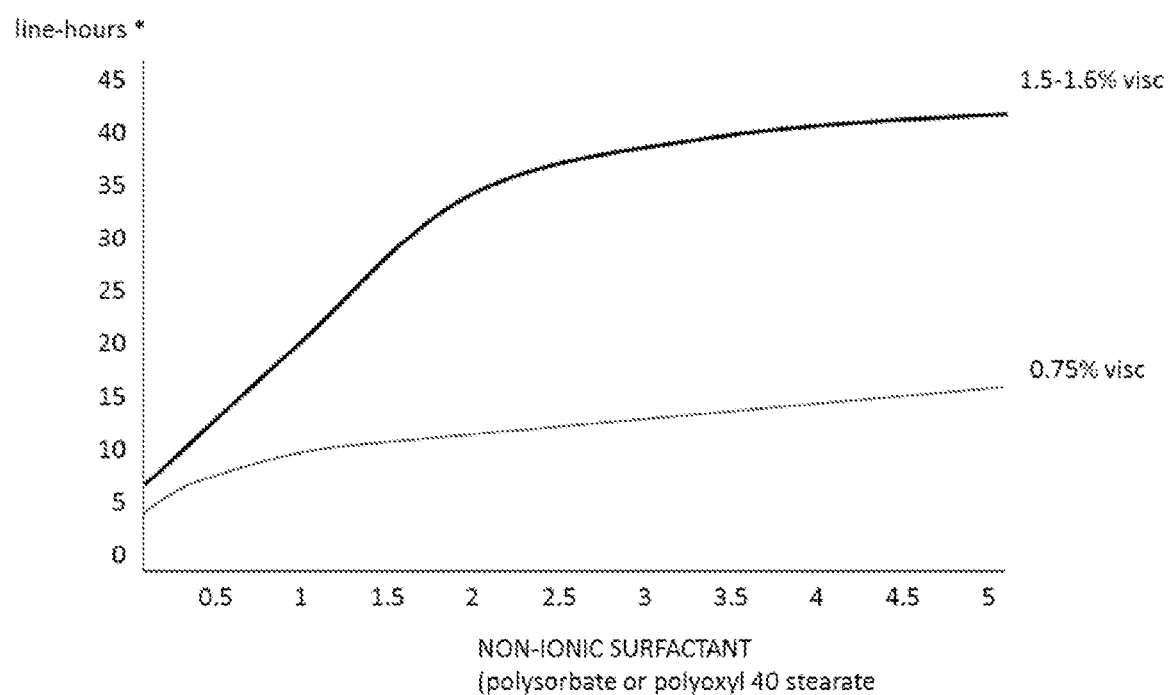
FIG. 3 is a graphical representation of the effects of addition of non-ionic surfactants and viscosity agents on near vision acuity and duration of effect. Line-Hours denotes lines improved times duration of effect.

The further addition of a viscosity agent by itself does not enhance duration. Surprisingly, the addition of a viscosity agent in a formulation with optimal ratios of aceclidine, tropicamide and a non-ionic surfactant dramatically improves duration. For example, a formulation of the present invention comprising 1.75% aceclidine, 2.5% mannitol, 0.01% tropicamide, 5% polysorbate 80 improves near vision in a presbyopic patient by up to 3 lines of vision acuity for about 4 to about 5 hours. The addition of 1.4% CMC further increases the near vision improvement to from about 7 to about 10 hours. Not to be held to a particular theory, a threshold above the critical micellar threshold greatly enhances permeation through the cornea by reducing micelle size from micrometers to nanometers. See FIG. 3.

Examples of compositions containing little or no cycloplegic agent are shown in Table 7 below.

TABLE 7

Compositions containing little or no cycloplegic agent

| | #L1 | #L2 | #L3 | #L4 | #L5 | #L6 | #L7 | #L8 | #L9 | #L10 |
|---|---|---|---|---|---|---|---|---|---|---|
| Aceclidine | 1.75% | 1.75% | 1.75% | 1.75% | 1.75% | 1.75% | 1.75% | 1.75% | 1.75% | 1.75% |
| Tropicamide | 0.02% | 0.02% | 0.02% | 0.02% | 0.02% | — | — | — | — | — |
| Mannitol | 2.5% | 2.5% | 2.5% | 2.5% | 2.5% | 2.5% | 2.5% | 2.5% | 2.5% | 2.5% |
| Polysorbate 80 | 0.75% | 0.25% | 0.25% | 0.1% | 0.1% | 0.5%* | 0.25% | 0.25% | 0.1% | 0.1% |
| Carbopol ® 940 or CMC | 0.95% | 0.95% | 0.95% | 0.9% | 0.95% | 0.95%* | 0.95%* | 0.95%* | 0.9%* | 0.95%* |
| Glycerine | | | | | | | | | | |
| Phosphate buffer | 3 mM | — | 3 mM | 3 mM | 3 mM | 3 mM | — | 3 mM | 3 mM | 3 mM |
| NaCl | 0.5% | 0.1% | 0.05% | — | 0.1% | 0.5%* | — | 0.05% | — | — |
| Boric acid | — | 0.12% | 0.2% | 0.2% | 0.12% | — | 0.12% | 0.2% | 0.2% | 0.12% |
| BAK | 0.015% | 0.01% | 0.01% | 0.05% | 0.01% | 0.015% | 0.01% | 0.01% | 0.05% | 0.01% |
| pH | 5.0 | 5.0 | 5.0 | 5.0 | 5.0 | 5.0 | 5.0 | 5.0 | 5.0 | 5.0 |

| | #L11 | #L12 | #L13 | #L14 | #L15 | #L16 | #L17 | #L18 | #L19 | #L20 | #L21 |
|---|---|---|---|---|---|---|---|---|---|---|---|
| Aceclidine | 1.65% | 1.65% | 1.75% | 1.75% | 1.65% | 1.65% | 1.75% | 1.75% | 1.75% | 1.75% | 1.75% |
| Tropicamide | 0.01% | 0.0275% | 0.020% | 0.025% | 0.025% | 0.025% | 0.025% | 0.025% | 0.025% | 0.015% | 0.015% |
| Mannitol | 2% | 2.5% | 2.5% | 2.5% | 2.50% | 2.50% | 2.5% | 2.50% | 2.50% | 2.50% | 2.5% |
| Polysorbate 80 | 2% | 2% | 1% | 0.10% | 2.50% | 2.50% | 3.00% | 2.50% | 2.50% | 2.50% | 2.50% |
| Carbopol ® 940 or CMC | 0.75% | 0.75% | 0.75% | 0.75% | 0.75% | 0.75% | 0.75% | 1.50% | 0.75% | 0.75% | 0.75% |
| Glycerine | 0.10% | 0.10% | 0.10% | 0.10% | 0.10% | 0.10% | 0.10% | 0.10% | 0.20% | 0.20% | 0.20% |
| Phosphate buffer | 3 mM | 3 mM | — | 3 mM | 3 mM | 3 mM | 3 mM | 3 mM | 3 mM | 3 mM | 3 mM |
| NaCl | | | | | | | | | | | |
| Boric acid | | | | | | | | | | | |
| BAK | 0.01% | 0.01% | 0.01% | 0.01% | 0.015% | 0.015% | 0.015% | 0.015% | 0.015% | 0.015% | 0.015% |
| pH | 5.0 | 5.0 | 5.0 | 5.0 | 5.25 | 5.25 | 5.25 | 5.25 | 5.25 | 5.25 | 5.25 |

| | #L22 | #L23 | #L24 | #L25 | #L26 | #L27 | #L28 | #L29 | #L30 | #L31 | #L32 |
|---|---|---|---|---|---|---|---|---|---|---|---|
| Aceclidine | 1.65% | 1.75% | 1.75% | 1.75% | 1.65% | 1.65% | 1.75% | 1.75% | 1.75% | 1.75% | 1.75% |
| Tropicamide | 0.025% | 0.0275% | 0.020% | 0.015% | 0.027% | 0.0275% | 0.0275% | 0.0275% | 0.025% | 0.022% | 0.0175% |
| Mannitol | 2.5% | 2.5% | 2.5% | 2.5% | 2.5% | 2.5% | 2.5% | 2.5% | 2.5% | 2.5% | 2.5% |
| Polysorbate 80 | 5% | 5% | 5% | 5% | 5% | 5% | 5% | 5% | | 5% | 5% |
| Carbopol ® 940 or CMC | 1.25% | 1.45% | 1.45% | 1.45% | 1.45% | 1.25% | 1.40% | 1.40% | 1.50% | 1.40% | 1.50% |
| Glycerine | | | | | | | | | | | |
| Phosphate buffer | 3 mM | 3 mM | 3 mM | 3 mM | 3 mM | 3 mM | 3 mM | 3 mM | 3 mM | 3 mM | 3 mM |
| NaCl | | | | | | | | | | | |
| Boric acid | | | | | | | | | | | |
| BAK | 0.01% | 0.01% | 0.01% | 0.01% | 0.01% | 0.01% | 0.01% | 0.01% | 0.01% | 0.01% | 0.01% |
| pH | 5.0 | 5.0 | 5.0 | 5.0 | 6.0 | 5.0 | 5.0 | 5.0 | 5.0 | 5.0 | 6.0 |
| Pupil Size (mm) | 3+ | 3+ | 3+ | 3+ | 3+ | 3+ | 3+ | 3+ | | | 3+ |
| Reading vs. Baseline 40 cm | | | | | | 7.0 | | 3+ | | | |
| Duration (hours) | 7 | 10+ | 10+ | 10+ | 10+ | 0.0 | 10+ | 10+ | | | 10+ |
| Ciliary Spasms | 0.0 | tr | 0.5 | 1.0 | 1.0 | | tr | 0.5 | | 1.0 | 1.0 |

TABLE 7-continued

Compositions containing little or no cycloplegic agent

| | #L33 | #L34 | #L35 | #L36 | #L37 | #L38 | #L47 | #L48 | #L49 | #L50 | #L51 |
|---|---|---|---|---|---|---|---|---|---|---|---|
| Aceclidine | 1.75% | 1.40% | 1.40% | 1.25% | 1.45% | 1.45% | 1.45% | 1.55% | 1.65% | 1.75% | 1.65% |
| Tropicamide | — | — | — | — | — | 0.0200% | — | 0.0200% | 0.0300% | 0.0300% | 0.0200% |
| Brimonidine | — | — | — | — | — | — | — | — | — | — | — |
| Mannitol | — | — | — | — | — | — | 2.5% | 4.0% | 2.5% | 2.5% | 2.5% |
| Polysorbate 80 | — | — | — | — | — | — | — | — | — | 5.00% | — |
| Polyoxyl 40 Stearate | — | — | — | — | 5.5% | 5.5% | 5.5% | 5.5% | 5.5% | — | 5.5% |
| Citrate | 0.10% | 0.10% | 0.10% | 0.10% | 0.10% | 0.10% | 0.10% | 0.10% | 0.10% | 0.10% | 0.10% |
| Glycerine | — | — | — | 0.10% | — | — | — | — | — | — | — |
| CMC | — | 1.45% | 0.75% | — | 0.85% | 0.75% | 0.75% | 0.75% | 0.75% | 0.75% | 0.75% |
| HPMC | 0.75% | — | — | — | — | — | — | — | — | — | — |
| Carbopol® 940 | — | — | — | — | — | — | — | — | — | — | — |
| NaCl | 0.75% | 0.75% | 0.50% | 0.50% | 0.50% | 0.50% | 0.50% | 0.50% | 0.50% | 0.50% | 0.00% |
| Boric Acid | — | — | — | — | — | — | — | — | — | — | — |
| Postassium Borate | — | — | — | — | — | — | — | — | — | — | — |
| Phosphate buffer | — | — | — | — | — | — | — | — | — | — | — |
| Acetate | 3 | 3 | 3 | 3 | 3 | 3 | 3 | 3 | 3 | 3 | 3 |
| pH | 5.0 | 5.0 | 5.0 | 5.0 | 5.0 | 5.0 | 5.0 | 5.0 | 5.25 | 5.0 | 5.0 |
| BAK | 0.015% | 0.015% | 0.015% | 0.015% | 0.015% | 0.015% | 0.015% | 0.015% | 0.015% | 0.015% | 0.015% |
| Pupil Size (mm) | 3 | 3.25 | 3 | 2 | 3 | 2.5 | 1.5 | 0.5 | 1.5 | 1.5 | 1 |
| Reading vs. Baseline 40 cm | 4 | 7 | 4.5 | — | 6.5 | 6 | 3 | 2 | 4 | 4 | 2 |
| Duration (hours) | 4 | 4 | 3 | 2 | 3 | 2 | 0.5 | 0.5 | 0.5 | 0.5 | 0.5 |
| Ciliary Spasms | 1.0 | — | 1.0 | — | 1.0 | 1.0 | 1 | 1 | 0.5 | 1 | 1 |
| Stinging | | | | | | | | | | | |
| Blur (min) | | | | | | | | | | | |
| Distance blur | none | none | none | none | none | none | none | none | none | none | none |
| Onset (min) | 20-11 | 20-12 | 20-13 | 20-14 | 20-15 | 20-16 | 20-25 | 20-25 | 20-25 | 20-25 | 20-25 |
| Redness 1 hr (0-4) | 2.0 | 4 | 1.5 | 0 | 0.5 | 0.5 | 0.5 | 0.5 | 0.5 | 0.5 | 0.5 |
| Redness 4 hr (0-4) | | | | | | | | | | | |
| Overall comfort | poor | poor | poor | fair | poor | poor | good | good | good | good | good |
| Osmolarity | hi | hi | hi | hi | hi | hi | hi | hi | hi | hi | hi |
| Efficacy index: read * dur | 12 | 23 | 14 | 0 | 20 | 15 | 5 | 1 | 6 | 6 | 2 |
| OVERALL (1-5) | * | **½ | * | — | * | ** | *** | * | * | * | * |

| | #L33 | #L34 | #L35 | #L36 | #L37 | #L38 | #L47 | #L48 | #L49 | #L50 | #L51 |
|---|---|---|---|---|---|---|---|---|---|---|---|
| Stinging | 0.5 | 0.5 | 0.5 | 0.5 | 0.5 | 0.5 | 0.5 | 0.5 | 0.5 | 0.5 | 0.5 |
| Blur (min) | 1 | 1 | 1 | 1 | 1 | 1 | 1 | 1 | 1 | 1 | 1 |
| Distance Blur | | | | | | | | | | | |
| Onset (min) | 20 | 20 | 20 | 20 | 20 | 20 | 20 | 20 | 20 | 20 | 20 |
| Redness 1 hr (0-4) | 0.5 | 0.5 | 0.5 | 0.5 | 0.5 | 0.5 | 0.5 | 0.5 | 0.5 | 0.5 | 0.5 |
| Redness 4 hr (0-4) | | | | | | | | | | | |
| Overall Comfort | sl sticky | sl sticky | sl sticky | sl sticky | sl sticky | sl sticky | sl sticky | sl sticky | sl sticky | sl sticky | sl sticky |
| Osmolarity | | | | | | | | | | | |
| Efficacy index: read * dur | | | | | | | | | | | |
| OVERALL (1-5) | best | best | best | best | best | best | best | best | best | best | best |

TABLE 7-continued

Compositions containing little or no cycloplegic agent

| | #L52 | #L53 | #L54 | #L55 | #L56 | #L57 | #L58 | #L59 | #L60 | #L61 | #L62 |
|---|---|---|---|---|---|---|---|---|---|---|---|
| Aceclidine | 1.65% | 1.65% | 1.65% | 1.75% | 1.75% | 1.65% | 1.65% | 1.65% | 1.65% | 1.65% | 1.75% |
| Tropicamide | 0.0100% | 0.0250% | 0.0000% | 0.0000% | 0.0250% | 0.0250% | 0.0250% | 0.0150% | 0.0400% | 0.0250% | 0.0300% |
| Brimonidine | — | — | — | — | — | — | — | — | — | — | — |
| Mannitol | 2.5% | 2.5% | 2.5% | 2.5% | 2.5% | 2.5% | 2.5% | 2.5% | 2.5% | 2.5% | 2.5% |
| Polysorbate 80 | 2.00% | 2.50% | 2.00% | 1.00% | 0.10% | 2.00% | 2.50% | 2.50% | 3.50% | 2.50% | 3.50% |
| Polyoxyl 40 Stearate | — | — | — | — | — | — | — | — | — | — | — |
| Citrate | — | 0.10% | — | — | — | — | — | — | — | — | — |
| Glycerine | 0.10% | 0.10% | 0.10% | 0.10% | 0.10% | 0.10% | 0.10% | 0.10% | 0.10% | 0.10% | 0.10% |
| CMC | 0.75% | 0.85% | 0.85% | 0.85% | 0.85% | 0.85% | 0.85% | 0.75% | 0.60% | 1.60% | 0.60% |
| HPMC | — | — | — | — | — | — | — | — | — | — | — |
| Carbopol® 940 | 0.50% | — | — | — | — | — | — | 0.75% | 0.60% | — | 0.60% |
| NaCl | — | 0.50% | — | — | — | — | — | — | — | — | — |
| Boric Acid | — | — | — | — | — | — | — | — | — | — | — |
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | — | — | — | — | — | — | — | — | — | — | — |
| pH | 5.0 | 5.0 | 5.0 | 5.3 | 5.3 | 5.3 | 5.00 | 5.00 | 5.00 | 5.00 | 5.00 |
| BAK | 0.015% | 0.015% | 0.015% | 0.015% | 0.015% | 0.015% | 0.015% | 0.015% | 0.015% | 0.015% | 0.015% |
| Pupil Size (mm) | 2.5 | 3 | 3 | 2 | 1.5 | 2.5 | 3 | 2 | 1.5 | 2.5 | 2.5 |
| Reading vs. Baseline 40 cm | 6 | 5 | 6 | 4 | 4 | 6 | 5.5 | 7 | 3 | 7 | 7 |
| Duration (hours) | 0 | 0.5 | 2 | 2 | 0 | 0 | 0 | 0.5 | 0 | 0.5 | 0.5 |
| Ciliary Spasms | 0.5 | 0.5 | 1 | 0.5 | 0.5 | 0.5 | 0.5 | 0.5 | 0.25 | 0.25 | 0.25 |
| Stinging | 1 | | | | | | | | 1.5 | 1 | 2 |
| Blur (min) | | | | | | | | | | | |
| Distance blur | none | none | none | none | none | none | none | none | none | none | none |
| Onset (min) | 20-25 | 20-25 | 20-25 | 20-25 | 20-25 | 20-25 | 20-25 | 20-25 | 20-25 | 20-25 | 20-25 |
| Redness 1 hr (0-4) | 0.5 | 0.5 | 0.5 | 0.5 | 1.0 | 0.5 | 0.5 | 0.5 | 0.5 | 0.5 | 0.5 |
| Redness 4 hr (0-4) | | | | | | | | | | | |
| Overall comfort | poor | poor | poor | poor | good | good | good | good | good | good | good |
| Osmolarity | hi | hi | nl | nl | nl | nl | nl | nl | nl | nl | nl |
| Efficacy index: read * dur | 15 | 15 | 18 | 8 | 6 | 15 | 17 | 14 | 5 | 18 | 18 |
| OVERALL (1-5) | ** | | | | | | | | | **** | **** |

| | #L63 | #L64 | #L65 | #L66 | #L67 | #L68 | #L69 | #L70 | #L71 | #L72 | #L73 |
|---|---|---|---|---|---|---|---|---|---|---|---|
| Aceclidine | 1.65% | 1.75% | 1.65% | 1.75% | 1.75% | 1.75% | 1.75% | 1.75% | 1.75% | 1.75% | 1.75% |
| Tropicamide | 0.0250% | 0.0250% | 0.0250% | 0.0275% | 0.0275% | 0.0275% | 0.0250% | 0.0180% | 0.0160% | 0.0160% | 0.0150% |
| Brimonidine | — | — | — | — | — | — | — | — | — | — | — |
| Mannitol | 2.5% | 2.5% | 2.5% | 2.5% | 2.5% | 2.5% | 2.5% | 2.5% | 2.5% | 2.5% | 2.5% |
| Polysorbate 80 | 2.50% | 3.50% | 4.00% | 5.00% | 5.00% | 2.00% | 2.00% | 2.00% | 2.25% | 4.00% | 4.00% |
| Polyoxyl 40 Stearate | — | — | — | — | — | — | — | — | — | — | — |
| Citrate | — | — | — | — | — | — | — | — | — | — | — |
| Glycerine | 0.10% | 0.10% | 0.10% | — | — | — | — | — | — | — | — |
| CMC | 0.75% | 0.50% | 0.75% | — | — | — | — | — | — | — | — |
| HPMC | — | — | — | 1.35% | 1.35% | 1.35% | 1.35% | 1.45% | 1.45% | 1.45% | 1.45% |
| Carbopol® 940 | — | — | — | — | — | — | — | — | — | — | — |
| NaCl | 0.50% | — | — | — | — | 1.45% | — | — | — | — | — |
| Boric Acid | — | — | — | — | — | — | — | — | — | — | — |

TABLE 7-continued

Compositions containing little or no cycloplegic agent

| | #L74 | #L75 | #L76 | #L77 | #L78 | #L79 | #L80 | #L81 | #L82 | #L83 | #L84 |
|---|---|---|---|---|---|---|---|---|---|---|---|
| Aceclidine | 1.75% | 1.75% | 1.75% | 1.75% | 1.75% | 1.75% | 1.75% | 1.75% | 1.75% | 1.65% | 1.40% |
| Tropicamide | 0.0150% | 0.0150% | 0.0120% | 0.0110% | 0.0100% | 0.0000% | — | 0.0100% | 0.0150% | 0.0000% | 0.0000% |
| Brimonidine | — | — | — | — | — | 0.015% | — | — | — | — | — |
| Mannitol | 2.5% | 2.5% | 2.5% | 2.5% | 2.5% | 2.5% | 2.5% | 2.5% | 2.5% | 2.5% | 2.5% |
| Polysorbate 80 | 5.00% | 5.00% | 5.00% | 5.00% | 5.00% | 5.00% | — | 6.00% | 7.00% | 0.00% | 0.00% |
| Polyoxyl 40 Stearate | — | — | — | — | — | — | — | — | — | — | 5.5% |
| Citrate | — | — | — | — | — | — | — | — | — | — | — |
| Glycerine | — | — | — | — | — | — | — | — | — | — | — |
| CMC | 1.45% | 1.43% | 1.43% | 1.40% | 1.40% | 1.40% | 1.40% | — | 1.40% | 0.00% | — |
| HPMC | — | — | — | — | — | — | — | — | — | — | — |
| Carbopol® 940 | — | — | — | — | — | — | — | — | 0.50% | — | — |
| NaCl | — | — | — | — | — | — | — | — | — | — | — |
| Boric Acid | — | — | — | — | — | — | — | — | — | — | — |
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | — | — | — | — | — | — | — | — | — | — | — |
| pH | 5.0 | 5.0 | 5.0 | 5.0 | 5.0 | 5.0 | 5.0 | 5.0 | 5.0 | 5.0 | 5.0 |
| BAK | 0.01% | 0.01% | 0.01% | 0.01% | 0.01% | 0.01% | 0.015% | 0.01% | 0.01% | 0.010% | 0.010% |
| Pupil Size (mm) | 3.25 | 3.25 | 3.5 | 3.5 | 3.75 | 2.5 | 2.5 | 2.75 | 2.5 | 1 | 1.5 |
| Reading vs. Baseline 40 cm | 7.5 | 7.5 | 7 | 8 | 9 | 8 | 7 | 5.5 | 5 | 3 | 3.5 |
| Duration (hours) | 0.5 | 0.5 | 1 | 1 | 1 | 2 | 2 | 0.5 | 0.5 | 1 | 1 |
| Ciliary Spasms | | | | | | | | | | | 1.0 |
| Stinging | | | | | | | | | | | |
| Blur (min) | 1.5 | 1.5 | 1.5 | | | | | | | | |

| | #L74 | #L75 | #L76 | #L77 | #L78 | #L79 | #L80 | #L81 | #L82 | #L83 | #L84 |
|---|---|---|---|---|---|---|---|---|---|---|---|
| Postassium Borate | — | — | — | — | — | — | — | — | — | — | — |
| Phosphate buffer | 3 | 3 | 3 | 3 | 3 | 3 | 3 | 3 | 3 | 3 | 3 |
| Acetate | 5.00 | 5.00 | 5.00 | — | — | — | — | — | — | — | — |
| pH | 0.015% | 0.015% | 0.015% | 5.0 | 5.0 | 5.0 | 5.0 | 5.0 | 5.0 | 5.0 | 5.0 |
| BAK | | | | 0.015% | 0.015% | 0.015% | 0.015% | 0.015% | 0.01% | 0.01% | 0.01% |
| Pupil Size (mm) | 2 | 2.5 | 2 | 2.75 | 2.75 | 2.75 | 2.75 | 2.75 | 2.75 | 2.75 | 3 |
| Reading vs. Baseline 40 cm | 4 | 0.5 | 5 | 7 | 7 | 5.5 | 6 | 7 | 7 | 7 | 7.5 |
| Duration (hours) | 0.5 | 0.5 | 0.5 | 0.5 | 0.5 | 0.5 | 0.5 | 0.5 | 0.5 | 0.5 | 0.5 |
| Ciliary Spasms | 0.5 | 0.5 | 0.5 | 0.5 | 0.5 | 0.5 | 0.5 | 0.5 | 0.5 | 0.5 | |
| Stinging | | | | | | | | | | | |
| Blur (min) | | | | | | | | | | 1 | |
| Distance blur | none | none | none | none | none | none | none | none | none | none | none |
| Onset (min) | 20-25 | 20-25 | 20-25 | 20-25 | 20-25 | 20-25 | 20-25 | 20-25 | 20-25 | 20-25 | 20-25 |
| Redness 1 hr (0-4) | 0.5 | 0.5 | 0.5 | | | 0.5 | | | | | |
| Redness 4 hr (0-4) | | | | | | | | | | | |
| Overall comfort | good | good | good | good | good | good | good | good | good | good | good |
| Osmolarity | nl | nl | nl | nl | nl | nl | nl | nl | nl | nl | nl |
| Efficacy index: read * dur | 8 | 0 | 10 | 19 | 19 | 15 | 17 | 19 | 19 | 19 | 23 |
| OVERALL (1-5) | poor | ? | **½ | **½ | ** | ** | | | | **** | ****½ |
| | #L74 | #L75 | #L76 | #L77 | #L78 | #L79 | #L80 | #L81 | #L82 | #L83 | #L84 |

TABLE 7-continued

Compositions containing little or no cycloplegic agent

| | #L85 | #L86 | #L87 | #L88 | #L89 | #L90 | #L91 | #L92 | #L93 | #L94 |
|---|---|---|---|---|---|---|---|---|---|---|
| Aceclidine | 1.75% | 1.75% | 1.75% | 1.75% | 1.75% | 1.75% | 1.75% | 1.75% | 1.75% | 1.75% |
| Tropicamide | 0.0000% | 0.0100% | 0.0900% | 0.0060% | 0.0060% | 0.0100% | 0.0060% | 0.0060% | 0.0060% | 0.0060% |
| Brimonidine | — | — | — | — | — | — | — | — | — | — |
| Mannitol | 2.5% | 2.5% | 2.5% | 2.5% | 2.5% | 2.5% | 2.5% | 2.5% | — | 2.5% |
| Polysorbate 80 | 5.00% | 2.5% | 2.5% | 2.5% | 2.5% | 2.50% | 2.50% | 2.75% | 2.75% | 3.50% |
| Polyoxyl 40 Stearate | — | — | — | — | — | — | — | — | — | — |
| Citrate | — | — | — | — | — | — | — | — | — | — |
| Glycerine | — | — | — | — | — | — | — | — | — | — |
| CMC | 1.40% | — | — | — | — | — | — | — | — | — |
| HPMC | — | 1.75% | 1.75% | 1.75% | 1.75% | — | — | — | — | — |
| Carbopol ® 940 | — | — | — | — | — | 1.75% | 1.75% | 1.80% | 1.80% | 1.80% |
| NaCl | 0.00% | 0.50% | — | 0.50% | — | 0.50% | 0.50% | 0.50% | 0.50% | 0.50% |
| Boric Acid | — | — | 0.35% | — | — | — | — | — | 0.25% | — |
| Postassium Borate | — | — | 0.47% | — | — | — | — | — | 0.37% | — |
| Phosphate buffer | — | — | — | — | 4 | — | — | — | — | — |
| Acetate | 3 | 3 | 3 | 3 | — | 3 | 3 | 3 | 3 | 3 |
| pH | 5.0 | 5.0 | 5.0 | 5.0 | 6.0 | 5.0 | 5.0 | 5.0 | 5.0 | 5.0 |
| BAK | 0.010% | 0.020% | 0.020% | 0.020% | 0.020% | 0.02% | 0.02% | 0.02% | 0.02% | 0.02% |
| Pupil Size (mm) | 3.5 | 3.5 | 3.5 | 3.75 | 3.75 | 3.5 | 3.75 | 3.75 | 3.75 | 3.75 |
| Reading vs. Baseline 40 cm | 7 | 8 | 7 | 9 | 9 | 7 | 7 | 8 | 8 | 8.5 |
| Duration (hours) | 2 | 0.5 | 0.5 | 0.5 | 0.5 | 0.5 | 0.5 | 0 | 0 | 0 |
| Ciliary Spasms | 0.5 | | | | | | | | | |
| Stinging | | | | | | | | | | |
| Blur (min) | | | | | | | | | | |
| Distance blur | 2.0 | none | none | none | none | none | none | none | none | none |
| Onset (min) | 20-25 | 20-25 | 20-25 | 20-25 | 20-25 | 20-25 | 20-25 | 20-25 | 20-25 | 20-25 |
| Redness 1 hr (0-4) | 1.0 | 1.0 | 0.5 | 0.5 | 0.5 | 0.5 | 0.5 | 0.5 | 0.5 | 0.5 |
| Redness 4 hr (0-4) | | | | | | | | | | 2.0 |
| Overall comfort | good-exc | good-exc | good-exc | good-exc | exc | exc | fair | good | good | fair |
| Osmolarity | nl | nl | nl | nl | nl | nl | nl | nl | nl | nl |
| Efficacy index: read * dur | 24 | 24 | 24 | 25 | 28 | 34 | 18 | 15 | 13 | 5 |
| OVERALL (1-5) | ***** | ***** | ***** | *****! | *****! | *****!! | **** | *** | *** | * |

TABLE 7-continued

Compositions containing little or no cycloplegic agent

| Overall comfort | good | good | good | good | good | | | |
|---|---|---|---|---|---|---|---|---|
| Osmolarity | nl | nl | nl | nl | lo | | | |
| Efficacy index: read * dur | 25 | 28 | 25 | 34 | 34 | 25 | 26 | 30 | 30 | 32 |
| OVERALL (1-5) | **** | | | | | ***** | ***** | ***** | ***** | ***** |

All concentration in weight by volume.
mm denotes millimeters.
cm denotes centimeters.
min denotes minutes.
%* denotes amount can optionally vary from about 0.01% to about 1% w/v.
# denotes formulation can include polysorbate 80 or not include polysorbate 80.
Ciliary spasms scores correspond to the following:
0 = no discomfort;
0.5 = slight sting;
1 = noticeable squeeze/discomfort;
2 = pain for less than 30 minutes;
3 = pain for 1 hour or more; and
4 = severe to intolerable pain.

Figure 4:
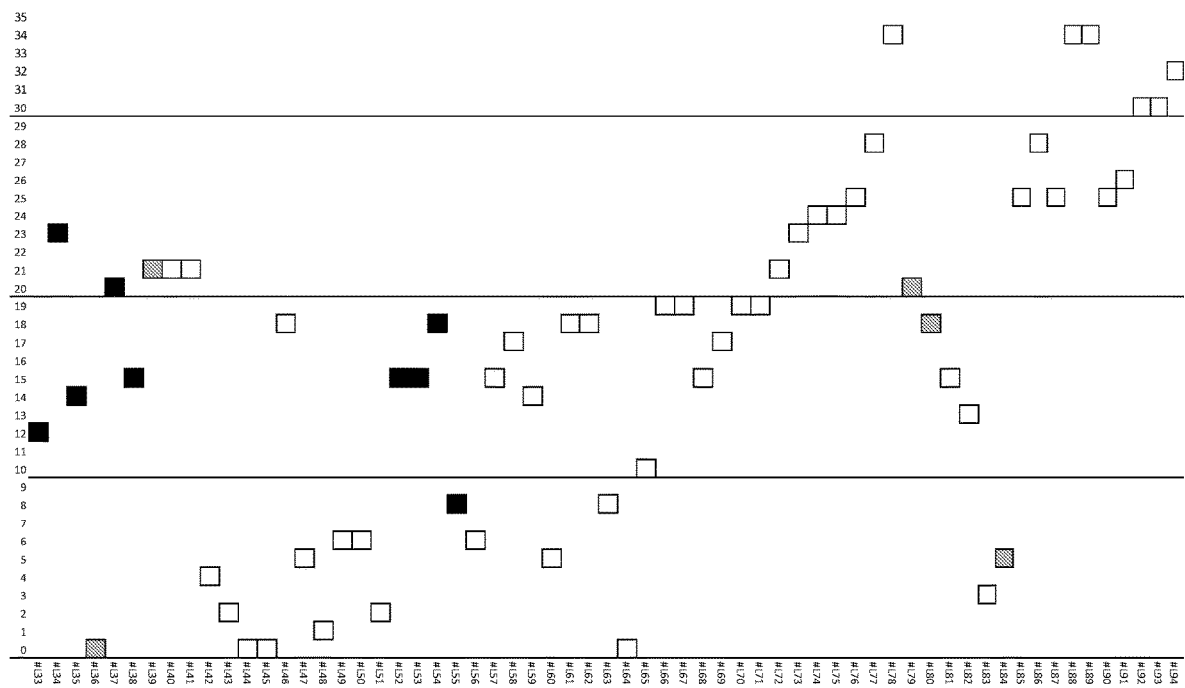
FIG. 4 is a graphical representation of the Efficacy Index for formulas #L33-#L94. Box color denotes a comfort level of good for white, fair for cross-hatched and poor for black.

The efficacy index is demonstrated in FIG. 4. In brief, the score is calculated by multiplying the lines of improvement in near visual acuity by the number of hours the improvement lasts. For example, a score of: 5 is equal to +1 lines of improvement in near visual acuity for 5 hours; 10 is equal to +1.5 lines of improvement for 6.7 hours; 15 is equal to 2 lines of improvement for 7.5 hours; 20 is equal to 2.5 lines of improvement for 8 hours; 25 is equal to 3+ lines of improvement for 8.3 hours and 35 is equal to 3.75+ lines of improvement for 9 hours.

As demonstrated by comparing the Reading vs. Baseline at 40 cm and Efficacy Indexes of formulas #L33-#L37, formulas containing 1.40% or more aceclidine are better at correcting presbyopia than those formulas containing 1.25% aceclidine. Inversely, the lower concentration of aceclidine results in better overall comfort to the user. The addition of 2.5% mannitol to formulas with 1.45% aceclidine improves overall comfort but at the expense of reducing the presbyopic correcting effect (compare #L37 with #L47.) This reduction in near vision improvement is exacerbated with the addition of 4.0% mannitol (compare #L47 with #L48.) Increasing aceclidine concentrations to 1.65% or 1.75% overcome the reduction in near vision improvement seen with the addition of mannitol (compare #L47 with #L49 and #L50.)

also inversely correlated with a decrease in tropicamide from 0.0275% to 0.01%. This same trend is demonstrated by the increase in effectiveness (i.e. Reading vs. Baseline 40 cm) when comparing #L85 through #L94.

This data demonstrates that mannitol can effectively reduce ciliary spasms caused by aceclidine, thus reducing the need for a cycloplegic agent such as tropicamide. Further, this data demonstrates that the addition of a non-ionic surfactant and viscosity agent can further enhance the efficacy and duration of compositions containing aceclidine, mannitol and low tropicamide. This data also demonstrates that the use of a cycloplegic agent in aceclidine compositions containing polysorbate 80 and CMC is most beneficial to presbyopic correction when the cycloplegic agent is closer to 0.006% than 0.025%. Finally, this data demonstrates that compositions comprising aceclidine and mannitol are sufficient to correct presbyopia with tolerable pain.

Example 8 Use of Further High Tropicamide Formulations

The following examples are of aceclidine formulations containing more than 0.03% tropicamide.

TABLE 8

| | High tropicamide formulations | | | | | | | |
|---|---|---|---|---|---|---|---|---|
| | #L39 | #L40 | #L41 | #L42 | #L43 | #L44 | #L45 | #L46 |
| Aceclidine | 1.45% | 1.45% | 1.40% | 1.40% | 1.40% | 1.40% | 1.40% | 1.40% |
| Tropicamide | 0.035% | 0.037% | 0.040% | 0.050% | 0.055% | 0.06% | 0.08% | 0.04% |
| Polyoxyl 40 Stearate | 5.5% | 5.5% | 5.5% | 5.5% | 5.5% | 5.5% | 5.5% | 5.5% |
| Citrate | 0.10% | 0.10% | 0.10% | 0.10% | 0.10% | 0.10% | 0.10% | 0.10% |
| Glycerine | 0.10% | 0.10% | 0.10% | 0.10% | 0.10% | 0.10% | 0.10% | 0.10% |
| CMC | 0.75% | 0.75% | 0.75% | 0.75% | 0.75% | 0.75% | 0.75% | 0.75% |
| NaCl | 0.50% | 0.50% | 0.50% | 0.50% | 0.50% | 0.50% | 0.50% | 0.50% |
| Phosphate buffer | 3 | 3 | 3 | 3 | 3 | 3 | 3 | 3 |
| pH | 5.0 | 5.0 | 5.0 | 5.25 | 5.5 | 5.25 | 5.0 | 5.0 |
| BAK | 0.015% | 0.015% | 0.015% | 0.015% | 0.015% | 0.015% | 0.015% | 0.015% |
| Reading vs. Baseline 40 cm | 3.5 | 3.5 | 3.5 | 2 | 1 | 1 | 1 | 3 |
| Duration (hours) | 6 | 6 | 6 | 2 | 2 | 1 | 1 | 6 |
| Ciliary Spasm | 1 | 0.5 | 0.5 | 0.5 | 0.5 | 0.5 | 0.5 | 0.5 |
| Stinging | 1.0 | 1.0 | 1.0 | 0.5 | 0.25 | 0.5 | 1 | 1 |
| Distance blur | none | none | none | none | none | none | none | none |
| Onset (min) | 20-17 | 20-18 | 20-19 | 20-20 | 20-21 | 20-22 | 20-23 | 20-24 |
| Redness 1 hr (0-4) | 0.5 | 0.5 | 0.5 | 0.5 | 0.5 | 0.5 | 0.5 | 0.5 |
| Overall comfort | fair | good | good | good | good | good | good | good |
| Osmolarity | hi | hi | hi | hi | hi | hi | hi | hi |
| Efficacy index: read * dur | 21 | 21 | 21 | 4 | 2 | 1 | 1 | 18 |
| OVERALL (1-5) | ** | *** | *** | * | ½* | ¼* | ¼* | *** |

Further, formulas containing 1.75% aceclidine and 2.5% mannitol have an increased efficacy and duration in treating presbyopia that is correlated with an increase in polysorbate 80 up to 5.0% and then inversely correlated with a decrease in CMC from 1.45% to 1.40% (compare formulas #L66 to #L78.) Optimal formulations are demonstrated by #L77, #L78 and #L85-#L94, which each have the highest improve reading at 40 cm at between 3.5 and 3.75 visual acuity lines and the highest Efficacy Index scores of 25 to 34, and the longest duration from 7 to 9 hours. The increase in effectiveness and duration of formulas from #L66 to #L78 are Ciliary spasms scores correspond to the following: 0=no discomfort; 0.5=slight sting; 1=noticeable squeeze/discomfort; 2=pain for less than 30 minutes; 3=pain for 1 hour or more; and 4=severe to intolerable pain.

As demonstrated by formulas #L39-#L41 and compared to formulas #L74-#L78 in Table 8, formulas containing about 1.40% to about 1.45% aceclidine, about 0.035% to about 0.04% tropicamide, about 5.5% polyoxyl 40 stearate and about 0.75% CMC are almost, but not quite as effective at treating presbyopia as formulas containing about 1.65% to about 1.75% aceclidine, about 2.5% mannitol, about 5% polysorbate 80, about 1.40% CMC formulas. This effectiveness decreases dramatically when tropicamide is increased to about 0.05% to about 0.08% tropicamide.

Example 9. Use of a Compound Containing Mannitol

Formulation:
aceclidine 1.75% w/v
tropicamide 0.006% w/v
mannitol 2.5% w/v
polysorbate 80 2.75% w/v
NaCl 0.5% w/v
hydroxypropylmethyl cellulose 0.5%-1.80% w/v
phosphate buffer 3 mM
pH 5.0, and
BAK 0.020% as preservative.
Method:
The subject instilled 2 drops of the above formulation in each eye and the excess wiped from lids and lashes.
Results:
Within 20 minutes, near vision improvement of about 3 lines of visual acuity was noted with very slight dimming. Throughout the day near vision remained enhanced with no loss of distance vision. Further, if the subject previously suffered from any mild refractive errors distance vision was improved. Over a 5-8 hour period the pupil begins to slightly recover, and after a few hours the minimal dimming was no longer noted. Both excellent near vision near onset, and possibly still slightly improved near vision continued as the pupil slightly begins to increase from its minimal size earlier in the day.

Example 10. Use of a Preferred Embodiment Optimizing Tropicamide and Hydroxypropyl Methyl Cellulose Composition

| | |
|---|---|
| Aceclidine | 1.75% w/v |
| Tropicamide | 0.010% w/v |
| Mannitol | 2.50% w/v |
| Polysorbate 80 | 3.50% w/v |
| NaCl | 0.50% w/v |
| HPMC | 1.25% w/v |
| BAK | 0.02% w/v |
| Phosphate buffer | 3 mM |
| pH | 5.00 |

Method
The subject instilled 2 drops of the above formulation in each eye as 1 single drop each eye and a second drop after 5 minutes.
Results:
Comfort, duration and efficacy were assessed. Stinging upon instillation and over the first hour was minimal with a score of 0.25 out of 4. Redness over the first hour was also minimal with a score of 0.5 out of 4 assessed at 20 minutes. Onset of vision improvement occurred with the first 20 to 25 minutes after instillation. Baseline near vision (i.e. 40 centimeters) was improved by 3.5 lines of visual acuity. Improvement in near vision lasted for 8.5 hours. Comparing this formula to those in Table 10, the Efficacy Index score was 29.75. Substituting HPMC 1.80% w/v with HPMC 1.65% w/v resulted in a slight reduction in near vision improvement to 3.25 lines of visual acuity and a slight reduction in duration to just over about 6 hour. Comparing this formula to those in Table 10, the Efficacy Index score was 19.5.

Example 11. Use of a Compound Containing Mannitol with Various Nonionic Surfactants Compositions Table 9 lists the active ingredients, excipients and their concentrations for compositions with both tested and prophetic examples of nonionic surfactants.
Methods
The subject independently instilled 2 drops of the above compositions in each eye and the excess wiped from lids and lashes.
Results
All nonionic surfactants tested demonstrate substantial near vision improvement. Of those tested only Brij® 35 polyoxyethylene glycol alkyl ether was marginal due to the significant corneal irritation, hyperemia and reduced duration that resulted. Polysorbate 80 and poly 35 castor oil were most preferred, polyoxyl 40 stearate and poloxamer 407 excellent as well. However, polyoxyl 40 stearate caused a precipitate reaction with cellulose viscosity agents and added other stability issues.
Comfort and duration for each non-ionic surfactant were also tested and are noted in Table 9. Stinging and Redness are based on a scale of 0 to 4 with 0 being none and 4 being the most severe. Other than Brij® 35 polyoxyethylene glycol alkyl ether stinging and redness were mild to nearly absent. Duration was excellent for each nonionic surfactant tested.

TABLE 9

Comparing efficacy and comfort of various nonionic surfactants

| % w/v | Polysorbate 80 | Polyoxyl 35 castor oil | Polyoxyl 40 stearate | Poloxamer 407 | Brij ® 35 | Tyloxapol (prophetic) | Polysorbate 20 (prophetic) | Polysorbate 188 (prophetic) | Solulan C-24 (prophetic) |
|---|---|---|---|---|---|---|---|---|---|
| Aceclidine | 1.75% | 1.75% | 1.75% | 1.75% | 1.75% | 1.75% | 1.75% | 1.75% | 1.75% |
| Tropicamide | 0.006% | 0.006% | 0.005% | 0.005% | 0.005% | 0.006% | 0.006% | 0.006% | 0.006% |
| Mannitol | 2.5% | 2.5% | 2.5% | 2.5% | 2.5% | 2.5% | 2.5% | 2.5% | 2.5% |
| Nonionic surfactant | 3.5% | 3.5% | 3.5% | 3.5% | 3.5% | 3.5% | 3.5% | 3.5% | 3.5% |
| NaCl | 0.50% | 0.50% | 0.50% | 0.50% | 0.50% | 0.50% | 0.50% | 0.50% | 0.50% |
| HPMC | 1.80% | 1.80% | 1.80% | 1.80% | 1.80% | 1.80% | 1.80% | 1.80% | 1.80% |
| BAK | 0.02% | 0.02% | 0.02% | 0.02% | 0.02% | 0.02% | 0.02% | 0.02% | 0.02% |
| Phosphate buffer | 3 mM | 3 mM | 3 mM | 3 mM | 3 mM | 3 mM | 3 mM | 3 mM | 3 mM |
| pH | 5.00 | 5.00 | 5.00 | 5.00 | 5.00 | 5.00 | 5.00 | 5.00 | 5.00 |
| Stinging | 0.25 | 0 | 0.5 | 0.5 | 2 | 0-2 | 0-2 | 0-2 | 0-2 |

TABLE 9-continued

Comparing efficacy and comfort of various nonionic surfactants

| % w/v | Poly-sorbate 80 | Polyoxyl 35 castor oil | Polyoxyl 40 stearate | Polo-xamer 407 | Brij ® 35 | Tyloxapol (prophetic) | Polysorbate 20 (prophetic) | Polysorbate 188 (prophetic) | Solulan C-24 (prophetic) |
|---|---|---|---|---|---|---|---|---|---|
| Redness 1 hr | 0.5 | 0.25 | 0.75 | 1 | 2.5 | 0.25-2.5 | 0.25-2.5 | 0.25-2.5 | 0.25-2.5 |
| Reading vs. Baseline (40 cm) | 3.75 | 3.5 | 3 | 3 | 2 | 2-3.5 | 2-3.5 | 2-3.5 | 2-3.5 |
| Duration (hours) | 10 | 9 | 7 | 7 | 4 | 4-8 | 4-8 | 4-8 | 4-8 |
| Efficacy Index read * dur | 37.5 | 31.5 | 21 | 21 | 8 | 8-37.5 | 8-37.5 | 8-37.5 | 8-37.5 |
| Onset (min) | 20-25 | 20-25 | 20-25 | 20-25 | 30-40 | 20-40 | 20-40 | 20-40 | 20-40 |

Example 12. Use of a Compound Containing Optimizing Nonionic Surfactant and Antioxidant Additives and Concentrations

| Compositions | |
|---|---|
| Aceclidine | 1.75% w/v |
| Tropicamide | 0.010% w/v |
| Mannitol | 2.50% w/v |
| Polysorbate 80 | 4.00% w/v |
| NaCl | 0.00% w/v |
| HPMC | 1.25% w/v (high MW equaling viscosity of about 400 cps units) |
| BAK | 0.02% w/v |
| Sorbate | 0.12% w/v |
| BAK | 0.02% w/v |
| EDTA | 0.01% |
| Citrate buffer | 3 mM |
| pH | 5.00 |

Method 2 subjects instilled 2 drops each of the above formulation in each eye about 5 minutes apart.

Results:

Comfort, duration and efficacy were assessed. Stinging upon instillation and over the first hour was minimal for each subject with a score of 0.50 out of 4 for about 15 seconds. Redness over the first hour was also minimal for each subject with a score of 0.25 out of 4 assessed at 20 minutes. Onset of vision improvement occurred with the first 20 to 25 minutes after instillation. For subject 1 baseline near vision (i.e. 40 centimeters) was improved by 4.0-4.25 lines of visual acuity and lasted for 11.5 hours. For subject 2 baseline near vision was improved by 3.5 lines of visual acuity and lasted for 9.5 hours. The Efficacy Index score was 47.38 and 33.25, among the highest achieved for any formulation.

Example 13. Aceclidine to Treat Presbyopia

Method

A 1.75% aceclidine in saline solution was formulated. One drop was instilled into each eye of a presbyopic subject. The visual acuity of the subject was tested both before and after instillation using a LogMAR chart.

Results

The subject recorded a best corrected distance visual acuity of LogMAR 0.50 at 45 centimeters near test card and LogMAR −0.12 best corrected distance acuity at 1-meter distance prior to instillation. After instillation the subject recorded a LogMAR score of 0.22 at 45 centimeters distance and maintained a −0.12 LogMAR score at 1-meter distance. This improved reading distance acuity was maintained for 3.5 hours post instillation. Noticeable degradation in reading distance acuity began at 4 hours post instillation.

Example 14. Aceclidine and Brimonidine to Treat Presbyopia (Hypothetical)

TABLE 10

Aceclidine and Brimonidine Formulation

| Formulation | AB#1 |
|---|---|
| Aceclidine | 1.75% |
| Brimonidine | 0.08% |
| Polysorbate 80 | 4.00% |
| Mannitol | 2.50% |
| HPMC | 1.25% |
| Sodium Citrate Anhydrous | 0.10% |
| Disodium Edetate Dihydrate | 0.10% |

Method

Formulation AB#1 was instilled via 2-drops with a 5-minute interval in the eyes of a 69-year-old male. The subject had a baseline of 20.60+/−2 ou. All near and distance vision with over-refraction was red-green adjusted to emmetropia. Near vision at 1 hour post instillation was measured. Further, duration to 20.40 vision was measured.

Results

Instillation of formulation AB#1 resulted in 20.25 (net 3.6 lines improvement) near vision at 1 hour post instillation. 20.40 vision lasted for at least XX hours post-instillation of AB#1. Thus, formulations containing 0.08% brimonidine resulted in correction of presbyopia with functional correction up to XX hours post-instillation.

Example 14. Brimonidine Effect on Pupil Constriction 3 different formulations as found in Table 11, below, were administered to the right eye of a 39-year-old subject with wash-out periods in between. Specifically on Days 1 and 3, 2 drops of formulation L1 was administered, on Days 2 and 7, 1 drop of formulation L2 was administered, on Day 5, 2 drops of formulation L2 was administered, and on Day 8, 2 drops of formulation L3 was administered. Pupil size was measured each day at 15 and 30 minutes and at 1, 2, 3 and 4 hours post administration.

TABLE 11

| Formulation | L1 | L2 | L3 |
|---|---|---|---|
| Aceclidine | 1.75% | 1.75% | 1.40% |
| Brimonidine | — | 0.08% | 0.08% |

TABLE 11-continued

| Formulation | L1 | L2 | L3 |
| --- | --- | --- | --- |
| Polysorbate 80 | 4.00% | 4.00% | 4.00% |
| Mannitol | 2.50% | 2.50% | 2.50% |
| HPMC | 1.25% | 1.25% | 1.25% |
| Sodium Citrate Anhydrous | 0.10% | 0.10% | 0.10% |
| Disodium Edetate Dihydrate | 0.10% | 0.10% | 0.10% |

Figure 5:
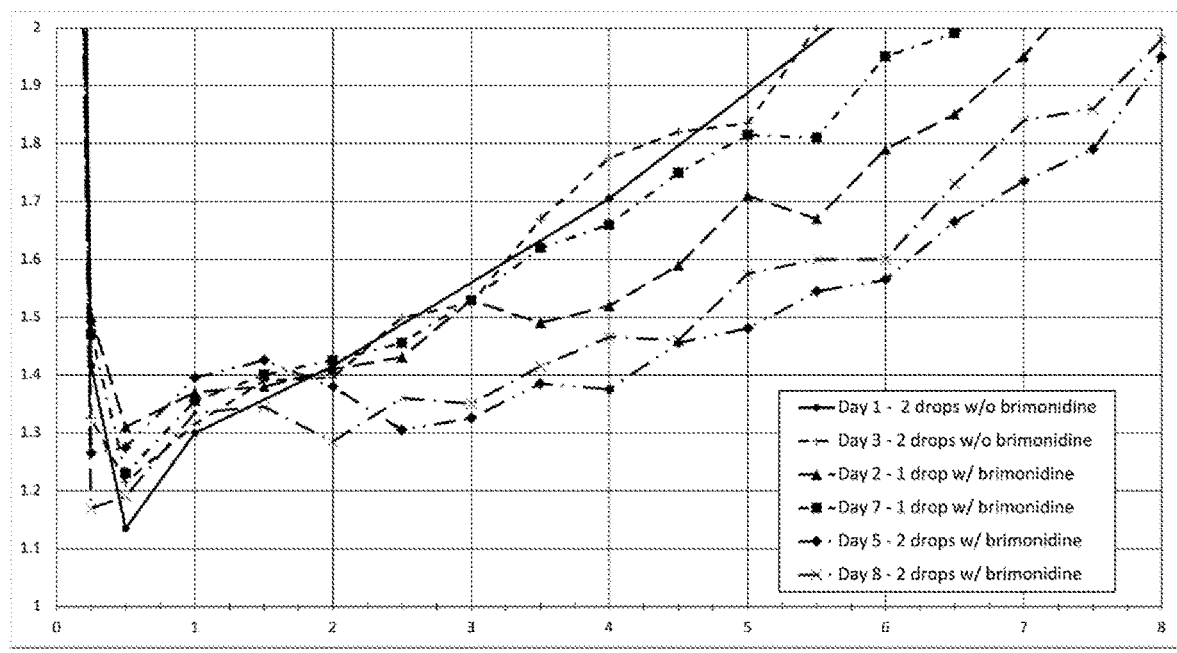
FIG. 5 is a graphical representation of pupil size over time following administration of formulas L1-L3.

As seen in FIG. 5, administration of 2 drops of formulations containing aceclidine or 1 or 2 drops of formulations containing aceclidine and brimonidine resulted in constriction of the pupil, which reached a minimum pupil size around 30 minutes post administration. The pupil size increased linearly following reaching minimum pupil size when the subject was administered either 2 drops of a formulation containing aceclidine or 1 drop of a formulation containing aceclidine and brimonidine. However, when 2 drops of formulations containing aceclidine and brimonidine were administered a $2^{nd}$ pupil constriction occurred around 2-2.5 hours post administration. The outcome of this $2^{nd}$ pupil constriction is that the subject maintained a pupil size ideal for correcting presbyopia (i.e. 1.5-1.8 mM) for a longer period of time.

What is claimed is:

1. A composition for the treatment of presbyopia comprising about 1.75% w/w aceclidine hydrochloride, about 0.08% w/w brimonidine or a salt thereof, about 4.0% w/w polysorbate 80, about 2.5% w/w mannitol, about 1.25% w/w hydroxypropylmethyl cellulose, about 0.1% w/w disodium edetate dihydrate and from about 0.06% to about 0.1% w/w anhydrous sodium citrate, wherein w/w denotes weight by total weight of the composition and wherein the composition has a pH from about 5.0 to about 5.75.

2. The composition of claim 1, wherein anhydrous sodium citrate is at a concentration of about 0.06% w/w.

3. The composition of claim 1, wherein anhydrous sodium citrate is at a concentration of about 0.08% w/w.

4. The composition of claim 1, wherein anhydrous sodium citrate is at a concentration of about 0.1% w/w.

5. A method of treating presbyopia comprising administering a composition comprising from about 1.75% w/w aceclidine hydrochloride, about 0.08% w/w brimonidine or a salt thereof, about 4.0% w/w polysorbate 80, about 2.5% w/w mannitol, about 1.25% w/w hydroxypropylmethyl cellulose, about 0.1% w/w disodium edetate dihydrate and from about 0.06% to about 0.1% w/w anhydrous sodium citrate to a subject in need thereof, wherein w/w denotes weight by total weight of the composition and wherein the composition has a pH from about 5.0 to about 5.75.

* * * * *